(12) United States Patent
Matheny

(10) Patent No.: US 10,864,233 B2
(45) Date of Patent: *Dec. 15, 2020

(54) COMPOSITIONS AND METHODS FOR TREATMENT OF CARDIOVASCULAR DISORDERS

(71) Applicant: CorMatrix Cardiovascular, Inc., Roswell, GA (US)

(72) Inventor: Robert G Matheny, Norcross, GA (US)

(73) Assignee: CorMatrix Cardiovascular, Inc., Roswell, GA (US)

(*) Notice: Subject to any disclaimer, the term of this patent is extended or adjusted under 35 U.S.C. 154(b) by 415 days.

This patent is subject to a terminal disclaimer.

(21) Appl. No.: 15/877,803

(22) Filed: Jan. 23, 2018

(65) Prior Publication Data

US 2018/0147241 A1    May 31, 2018

Related U.S. Application Data

(63) Continuation-in-part of application No. 15/681,731, filed on Aug. 21, 2017, and a continuation of application No. 14/644,476, filed on Mar. 11, 2015, now Pat. No. 9,737,569, and a continuation of application No. 13/782,115, filed on Mar. 1, 2013, now Pat. No. 9,119,899, and a continuation-in-part of application No. 13/573,569, filed on Sep. 24, 2012, now Pat. No. 9,072,816, and a continuation-in-part of application No. 13/328,287, filed on Dec. 16, 2011, now Pat. No. 9,532,943.

(51) Int. Cl.

| | | |
|---|---|---|
| A61K 35/34 | (2015.01) | |
| A61K 45/06 | (2006.01) | |
| A61K 48/00 | (2006.01) | |
| A61K 35/35 | (2015.01) | |
| A61K 35/12 | (2015.01) | |
| A61L 27/36 | (2006.01) | |
| A61K 38/18 | (2006.01) | |
| A61L 27/38 | (2006.01) | |
| A61L 27/54 | (2006.01) | |
| A61M 1/12 | (2006.01) | |
| A61K 35/28 | (2015.01) | |
| A61P 9/10 | (2006.01) | |
| A61K 35/44 | (2015.01) | |

(52) U.S. Cl.
CPC .............. *A61K 35/35* (2013.01); *A61K 35/12* (2013.01); *A61K 35/28* (2013.01); *A61K 35/34* (2013.01); *A61K 35/44* (2013.01); *A61K 38/18* (2013.01); *A61K 38/185* (2013.01); *A61K 38/1808* (2013.01); *A61K 38/1841* (2013.01); *A61K 38/1866* (2013.01); *A61K 45/06* (2013.01); *A61K 48/00* (2013.01); *A61L 27/3604* (2013.01); *A61L 27/367* (2013.01); *A61L 27/3629* (2013.01); *A61L 27/3633* (2013.01); *A61L 27/3826* (2013.01); *A61L 27/3834* (2013.01); *A61L 27/54* (2013.01); *A61M 1/122* (2014.02); *A61P 9/10* (2018.01); *A61L 2300/414* (2013.01); *A61L 2300/434* (2013.01); *A61L 2300/64* (2013.01); *A61L 2430/20* (2013.01); *A61M 2205/05* (2013.01)

(58) Field of Classification Search
None
See application file for complete search history.

(56) References Cited

U.S. PATENT DOCUMENTS

| | | | | |
|---|---|---|---|---|
| 9,539,410 B2* | 1/2017 | Basu | ................. | A61K 9/0019 |
| 2015/0297798 A1* | 10/2015 | Badylak | ................. | A61L 31/06 |
| | | | | 600/37 |
| 2017/0100523 A1* | 4/2017 | Matheny | ................. | A61L 27/18 |

OTHER PUBLICATIONS

Yu, et al. Exosomes Derived from Mesenchymal Stem Cells; 2014, Int J Mol Sci.; vol. 15(3); pp. 4142-57.*

* cited by examiner

*Primary Examiner* — Maria G Leavitt
(74) *Attorney, Agent, or Firm* — Francis Law Group

(57) ABSTRACT

Methods for treating cardiovascular disorders that include administration of an ECM based composition to damaged cardiovascular tissue in conjunction with a treatment remedy, such as ventricular assistance and transmyocardial revascularization (TMR), which induces enhanced bioremodeling of the damaged cardiovascular tissue and regeneration of new cardiovascular tissue and associated structures with site-specific structural and functional properties.

9 Claims, 14 Drawing Sheets

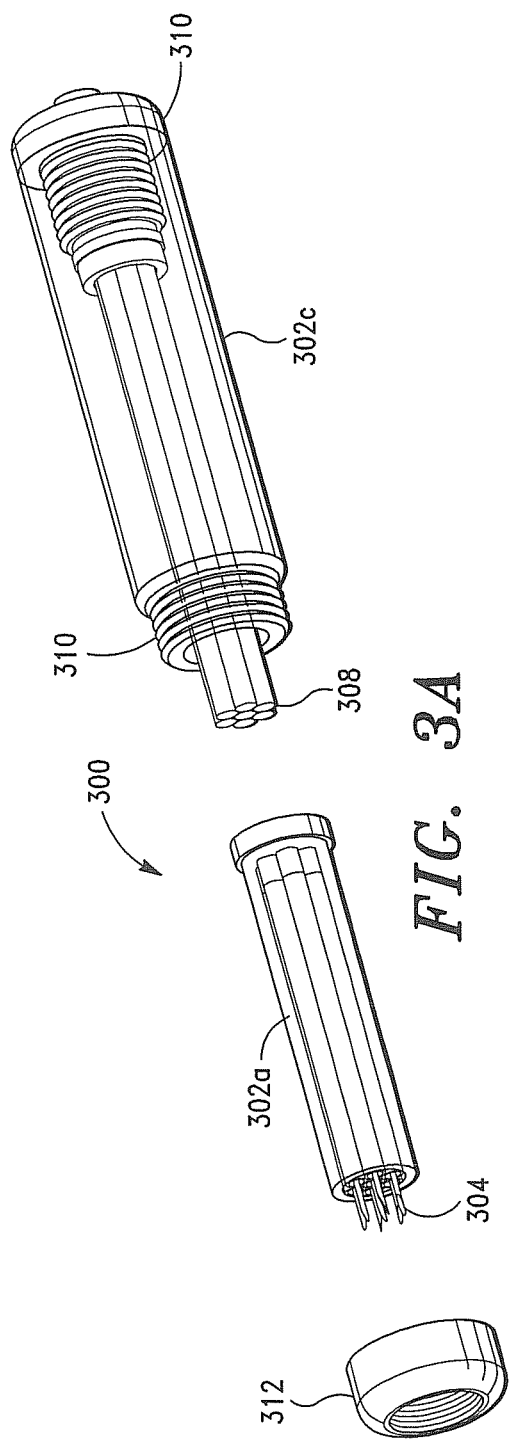
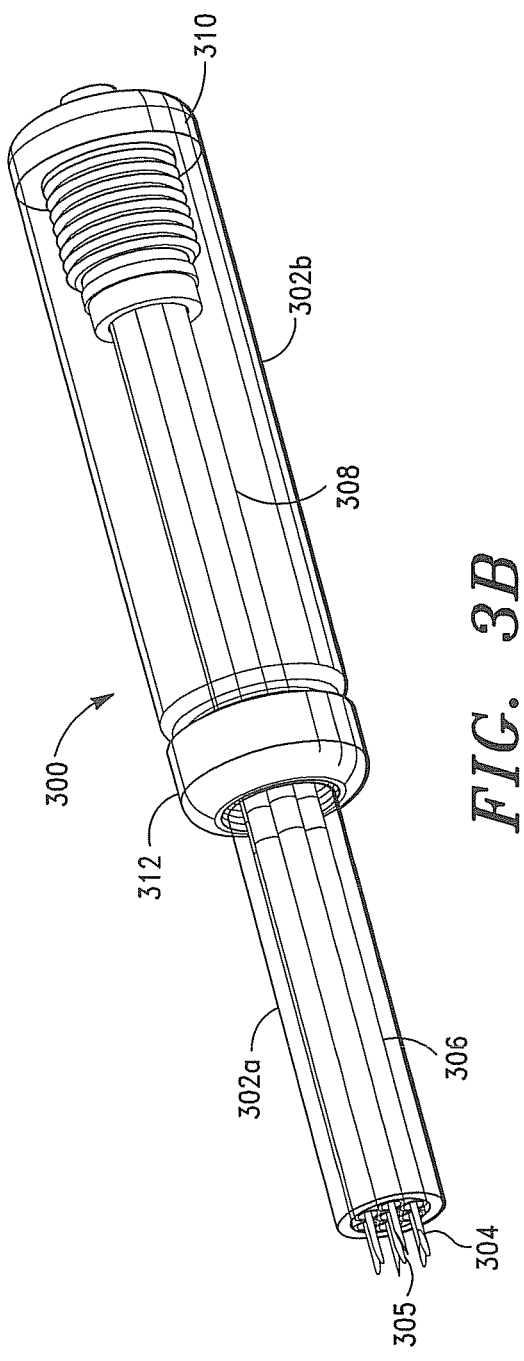

COMPOSITIONS AND METHODS FOR TREATMENT OF CARDIOVASCULAR DISORDERS

CROSS-REFERENCES TO RELATED APPLICATIONS

This application is a continuation-in-part of U.S. application Ser. No. 15/681,731, filed on Aug. 21, 2017, which is a continuation of U.S. application Ser. No. 14/644,476, filed on Mar. 11, 2015, now U.S. Pat. No. 9,737,569, which is a continuation of U.S. application Ser. No. 13/782,115, filed on Mar. 1, 2013, now U.S. Pat. No. 9,119,899, which is a continuation-in-part of U.S. application Ser. No. 13/573,569, filed on Sep. 24, 2012, now U.S. Pat. No. 9,072,816, which is a continuation-in-part of U.S. application Ser. No. 13/328,287, filed on Dec. 16, 2011, now U.S. Pat. No. 9,532,943, which claims the benefit of U.S. Provisional Application No. 61/425,172, filed on Dec. 20, 2010.

FIELD OF THE INVENTION

The present invention relates to methods for treating cardiovascular disorders. More particularly, the present invention relates to extracellular matrix (ECM) compositions and methods for treating cardiovascular disorders.

BACKGROUND OF THE INVENTION

As is well known in the art, heart failure can be caused by a diverse array of cardiovascular disorders that reduce the efficiency of the myocardium, including ischemic heart disease, coronary artery disease, and a defective or diseased heart valve. Among the noted disorders, ischemic heart disease, which commonly presents as a myocardial infarction, is the leading cause of heart failure. In 2017, 8.5 million people will have CHF and it is expected to grow by 46% by 2030. (AHA 2017 Heart disease and Stroke Statistics Update).

Indeed, in 2004 alone, the World Health Organization estimated that 12.2% of worldwide deaths occurred as a result of ischemic heart disease. Ischemic heart disease was also deemed the leading cause of death in middle to high income countries and second only to respiratory infections in lower income countries. *The Global Burden of Disease: World Health Organization* 2004 *Update*, Geneva (2008). Worldwide more than 3 million people present with a ST elevation myocardial infarction (STEMI) and 4 million people present with a non-ST elevation myocardial infarction (NSTEMI) a year. White, et al., *Acute Myocardial Infarction*, Lancet 372 (9638), pp. 570-84 (August 2008).

Rates of death from ischemic heart disease have slowed or declined in most high income countries, although cardiovascular disease still accounted for 1 in 3 of all deaths in the USA in 2008. Roger, et al., *Executive summary: Heart Disease and Stroke Statistics—2012 update: A report from the American Heart Association*, Circulation 125 (1), pp. 188-97 (January 2012).

In contrast, ischemic heart disease is becoming a more common cause of death in the developing world. For example in India, ischemic heart disease had become the leading cause of death by 2004; accounting for 1.46 million deaths (14% of total deaths). Deaths in India due to ischemic heart disease were also expected to double during 1985-2015. Gupta, et al., *Epidemiology and Causation of Coronary Heart Disease and Stroke in India*, Heart 94 (1), pp. 16-26 (January 2008).

Globally, it is predicted that disability adjusted life years (DALYs) lost to ischemic heart disease will account for 5.5% of total DALYs in 2030, making it the second most important cause of disability (after unipolar depressive disorder), as well as the leading cause of death by this date.

Ischemic heart disease often occurs when myocardial tissue is no longer receiving adequate blood flow. Various methods for treating ischemic heart disease have thus been developed. Such methods include systemic delivery of various pharmacological agents.

Several additional methods for treating ischemic heart disease are directed to re-establishing blood flow to the ischemic area. Such methods include stimulation of angiogenesis and surgical intervention, e.g. bypass surgery or angioplasty. Other methods include the use of lasers to bore holes through the ischemic area(s) to promote blood flow. As one can readily appreciate, there are numerous incumbent risks associated with the noted methods.

A further method for treating ischemic heart disease is the direct delivery of bioactive or pharmacological agents to the ischemic area. Illustrative are the extracellular matrix (ECM) based compositions disclosed in U.S. Pat. Nos. 8,784,891, 8,734,842, 8,734,841; 8,753,885, 8,795,728, 8,980,296 and 9,072,816 and Co-pending application Ser. Nos. 15/681,731, 15/386,902 and 15/386,960.

More recently, ventricular assist devices (VADs) have been employed as treatment platforms for various pharmacological therapies, e.g. stem cell administration, which have been developed to treat cardiovascular disorders, including ischemic heart disease. VADs are designed to support (or augment) the function of either the right (RVAD) or left (LVAD) ventricle, or both at once (BiVAD). The type of VAD employed depends primarily on the underlying cardiovascular disorder, and the pulmonary arterial resistance that determines the load on the right ventricle.

Use of VADs in conjunction with the delivery of ECM based compositions, such as disclosed in Applicant's U.S. Pat. Nos. 9,119,899, 8,871,511, 9,161,952, 9,265,798, 9,265,799 and 9,327,000, have also been found effective in treating various cardiovascular disorders, including ischemic heart disease.

Although the direct delivery of bioactive and pharmacological agents, and other treatment therapies have been found effective to treat cardiovascular disorders and, thereby, heart failure, there remains a need to provide even more effective means for treating cardiovascular disorders.

It is therefore an object of the present invention to provide improved bioactive compositions and methods for treating damaged or diseased biological tissue; particularly, cardiovascular tissue and, hence, cardiovascular disorders associated therewith.

It is another an object of the present invention to provide improved ECM based compositions that promote tissue survival, and induce neovascularization and regeneration of damaged cardiovascular tissue.

It is yet another object of the present invention to provide methods for treating cardiovascular disorders that include administration of improved ECM based compositions, which, when delivered to damaged cardiovascular tissue, induce neovascularization, host tissue proliferation, bioremodeling of the damaged cardiovascular tissue, and regeneration of new cardiovascular tissue and associated structures with site-specific structural and functional properties.

It is yet another object of the present invention to provide methods for treating cardiovascular disorders that include administration of an ECM based composition to damaged cardiovascular tissue in conjunction with a treatment remedy, such as ventricular assistance and/or transmyocardial revascularization (TMR), which induces enhanced bioremodeling of the damaged cardiovascular tissue and regeneration of new cardiovascular tissue and associated structures with site-specific structural and functional properties.

SUMMARY OF THE INVENTION

The present invention is directed to ECM based compositions and methods for treating damaged or diseased biological tissue.

In a preferred embodiment of the invention, the improved ECM based compositions comprise decellularized ECM derived from a mammalian tissue source, including, without limitation, small intestine submucosa (SIS), urinary bladder submucosa (UBS), stomach submucosa (SS), cardiovascular tissue, mesothelial tissue and placental tissue.

In some embodiments, the ECM based compositions further include at least one exogenously added biologically active agent that supports the treatment of damaged cardiovascular tissue and/or bioremodeling and/or regeneration of tissue.

In some embodiments of the invention, the biologically active agent comprises growth factor, such as, without limitation, basic fibroblast growth factor (bFGF), transforming growth factor beta (TFG-β) and vascular epithelial growth factor (VEGF).

In some embodiments of the invention, the biologically active agent comprises an exosome.

In some embodiments, the exosome comprises a MSC derived exosome.

In some embodiments of the invention, the exosome is derived from amniotic membrane, placenta, amniotic fluid and Whartons jelly.

In some embodiments, the exosome comprises a synthetically modified exosome.

In some embodiments, the synthetically modified exosome comprises a mesenchymal stem cell (MSC) derived synthetically modified exosome.

In some embodiments, the MSC derived synthetically modified exosome comprises an encapsulated growth factor selected from the group consisting of bFGF, TGF-β, and VEGF.

In some embodiments, the MSC derived synthetically modified exosome comprises an encapsulated inflammation modulating agent selected from the group consisting of a cytokine, transcription factor RNA and micro RNA (miRNA).

In some embodiments of the invention, the ECM based compositions are formulated to facilitate injection of the ECM based compositions to damaged or diseased tissue (i.e. injectable compositions).

In some embodiments of the invention, the ECM based compositions are in the form of a graft.

In some embodiments of the invention, the ECM based compositions are administered or delivered in conjunction with ventricular assistance via a ventricular assist device (VAD), pacemaker or other device adapted to support cardiovascular function.

In some embodiments of the invention, the ECM based compositions are administered or delivered in conjunction with transmyocardial revascularization (TMR) via a TMR device adapted to induce revascularization and/or angiogenesis in tissue.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 3A is an exploded perspective view of one embodiment of a multi-needle injection apparatus that is suitable for direct administration of ECM compositions to an ischemic infarcted region, in accordance with the invention;

FIG. 3B is an assembled perspective view of the multi-needle injection apparatus shown in FIG. 3A, in accordance with the invention;

DETAILED DESCRIPTION OF THE PREFERRED EMBODIMENT

Figure 1:
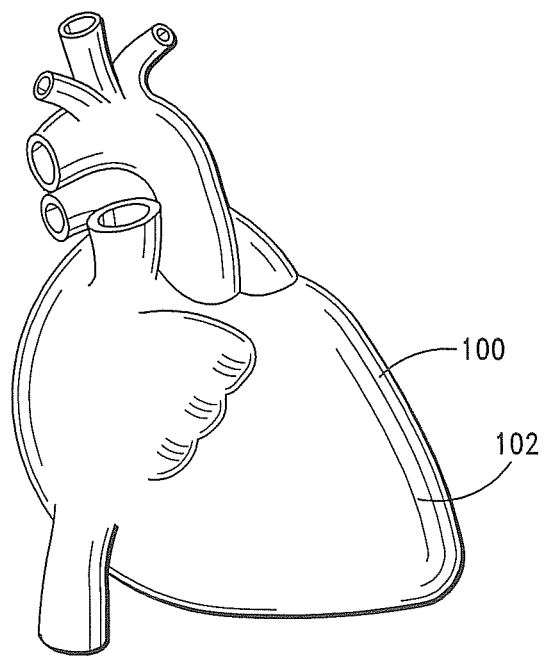
FIG. 1 is a depiction of a normal heart.

Before describing the present invention in detail, it is to be understood that this invention is not limited to particularly exemplified apparatus, systems, compositions or methods as such may, of course, vary. Thus, although a number of apparatus, systems, compositions and methods similar or equivalent to those described herein can be used in the practice of the present invention, the preferred apparatus, systems, compositions and methods are described herein.

It is also to be understood that, although a preferred method of delivering an ECM based composition of the invention to biological tissue comprises direct injection into the tissue, the delivery of an ECM based composition is not limited to direct injection. According to the invention, an ECM based composition of the invention can be delivered to biological tissue via a prosthetic construct, e.g. graft, and by other conventional means, including topical administration.

It is further to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference herein in their entirety.

Finally, as used in this specification and the appended claims, the singular forms "a, "an" and "the" include plural referents unless the content clearly dictates otherwise. Thus, for example, reference to "an anti-inflammatory" includes two or more such agents and the like.

DEFINITIONS

The terms "cardiovascular disorder" and "heart failure" are used interchangeably herein, and mean and include any abnormal function of the heart; particularly, abnormal functions or deficiency of the myocardium. The terms "cardiovascular disorder" and "heart failure" thus include, without limitation, ischemic heart disease, coronary artery disease, a defective or diseased heart valve, myocarditis, an inflammatory disease, cardiomyopathy and amyloidosis.

The terms "cardiovascular tissue damage," "cardiac tissue damage," and "cardiac tissue injury" and are used interchangeably herein, and mean and include any area of abnormal tissue in the cardiovascular system or heart caused by a disease, disorder, injury or damage, including damage to the epicardium, endocardium and/or myocardium.

As is well known in the art, cardiovascular tissue damage most often involves damage or injury to the myocardium and, therefore, for the purposes of this disclosure, myocardial damage or injury is equivalent to cardiovascular tissue damage.

The terms "extracellular matrix", "ECM" and "ECM material" are used interchangeably herein, and mean and include a collagen-rich substance that is found in between cells in mammalian tissue, and any material processed therefrom, e.g. decellularized ECM. According to the invention, ECM can be derived from a variety of mammalian tissue sources, including, without limitation, small intestine submucosa (SIS), urinary bladder submucosa (UBS), stomach submucosa (SS), central nervous system tissue, epithelium of mesodermal origin, i.e. mesothelial tissue, dermal tissue, subcutaneous tissue, gastrointestinal tissue, i.e. large and small intestine tissue, tissue surrounding growing bone, placental tissue, omentum tissue, cardiac tissue, e.g., pericardium and/or myocardium tissue, kidney tissue, pancreas tissue, lung tissue, and combinations thereof. The ECM can also comprise collagen from mammalian sources.

ECM can also be derived from basement membrane of mammalian tissue/organs, including, without limitation, urinary basement membrane (UBM), liver basement membrane (LBM), and amnion, chorion, allograft pericardium, allograft acellular dermis, amniotic membrane, Wharton's jelly, and combinations thereof.

The term "chamber remodeling", as used herein, means and includes a series of events (which may include changes in gene expression, molecular, cellular and interstitial changes) that result in changes in size, shape and function of biological tissue following stress or injury. As is well known in the art, remodeling can occur after a myocardial infarction, pressure overload (e.g., aortic stenosis, hypertension), volume overload (e.g., valvular regurgitation), inflammatory heart disease (e.g., myocarditis), or in idiopathic cases (e.g., idiopathic dilated cardiomyopathy).

The term "angiogenesis", as used herein, means a physiologic process involving the growth of new blood vessels from pre-existing blood vessels.

The term "neovascularization", as used herein, means and includes the formation of functional vascular networks that can be perfused by blood or blood components. Neovascularization includes angiogenesis, budding angiogenesis, intussusceptive angiogenesis, sprouting angiogenesis, therapeutic angiogenesis and vasculogenesis.

The term "revascularization", as used herein, thus means and includes the reformation (or restoration) of functional vascular networks that can be perfused by blood or blood components. Revascularization similarly includes angiogenesis, budding angiogenesis, intussusceptive angiogenesis, sprouting angiogenesis, therapeutic angiogenesis and vasculogenesis.

The terms "pharmacological agent", "pharmacological composition" and "biologically active agent", as used herein, mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent" and "biologically active agent" thus mean and include one of the agents disclosed in U.S. application Ser. No. 14/644,476, including, without limitation, the disclosed antibiotics, anti-arrhythmic agents, anti-viral agents, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPS), enzymes and enzyme inhibitors, anticoagulants and/or anti-thrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "biologically active agent" and "biologically active composition" also mean and include an "exosome."

The terms "exosome," "microsome" and "micro-vesicle" are used interchangeably herein, and mean and include a micellar body formed from a hydrocarbon monolayer or bilayer configured to contain or encase a composition of matter, such as a pharmacological agent and/or biologically active agent.

The terms "exosome", "microsome" and "micro-vesicle" thus include, without limitation, a micellar body formed from a lipid layer configured to contain or encase biologically active agents and/or combinations thereof.

According to the invention, the terms "pharmacological agent" and "biologically active agent" further include, without limitation, the following growth factors: platelet derived growth factor (PDGF), epidermal growth factor (EGF), transforming growth factor alpha (TGF-alpha), transforming growth factor beta (TGF-beta), fibroblast growth factor-2 (FGF-2), basic fibroblast growth factor (bFGF), vascular epithelial growth factor (VEGF), hepatocyte growth factor (HGF), insulin-like growth factor (IGF), nerve growth factor (NGF), tumor necrosis factor alpha (TNA-alpha), and placental growth factor (PLGF).

The term "biologically active agent" further includes, without limitation, organisms that have the potential to induce modulating proliferation, and/or growth and/or regeneration of tissue. The term "biologically active agent" thus includes, without limitation, the following cells: human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogeneic cells, allogeneic cells, and post-natal stem cells.

The terms "ECM composition" and "ECM based composition" are used interchangeably herein and mean and include a composition comprising at least one ECM material, and/or a "biologically active agent" and/or "pharmacological agent" and/or any additional agent or component identified herein.

The term "therapeutically effective", as used herein, means that the amount of the "ECM composition" and/or "ECM based composition" and/or "biologically active agent" and/or "pharmacological agent" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "prevent" and "preventing" are used interchangeably herein, and mean and include reducing the frequency or severity of a disease, condition or disorder. The term does not require an absolute preclusion of the disease, condition or disorder. Rather, this term includes decreasing the chance for disease occurrence.

The terms "treat" and "treatment" are used interchangeably herein, and mean and include medical management of a patient with the intent to cure, ameliorate, stabilize, or prevent a disease, pathological condition or disorder. The terms include "active treatment", i.e. treatment directed specifically toward the improvement of a disease, pathological condition or disorder, and "causal treatment", i.e. treatment directed toward removal of the cause of the associated disease, pathological condition or disorder.

The terms "treat" and "treatment" further include "palliative treatment", i.e. treatment designed for the relief of symptoms rather than the curing of the disease, pathological condition or disorder, "preventative treatment", i.e. treatment directed to minimizing or partially or completely inhibiting the development of the associated disease, pathological condition or disorder, and "supportive treatment", i.e. treatment employed to supplement another specific therapy directed toward the improvement of the associated disease, pathological condition or disorder.

The tennis "inciting event" and "tissue inciting event" are used interchangeably herein, and mean and include any event or action that induces a biological insult or biological tissue damage and, thereby, cellular migration and/or a release of cytokines, including growth factors and/or other bioactive molecules, and/or other cellular activities that are associated with inflammation modulation and/or stem cell proliferation and/or neovascularization.

The terms "inciting event" and "tissue inciting event" thus include, without limitation, induced (i) mechanical and pneumatic tissue trauma, e.g., piercing, tearing, blunt force, friction, etc., (ii) tissue hypoxia, (iii) tissue inflammation, e.g. delivery of antigens or cytotoxic neoplastics, (iv) chemically-induced tissue damage, (v) temperature-induced tissue damage, (vi) irradiation, e.g. laser radiation, ultrasonic radiation, etc., (vii) tissue compression, e.g. venous hypertension, and (viii) disruption of cell homeostasis, e.g. starving tissue of a seminal nutrient.

The terms "transmyocardial revascularization" and "TMR" are used interchangeably herein, and mean and include inducing revascularization and/or angiogenesis in a cardiovascular structure or tissue associated therewith by transmitting external energy to the cardiovascular structure or tissue, wherein the tissue structure is disrupted and, in at least one aspect, a volumetric void or cavity is generated in the cardiovascular structure.

As discussed in detail herein, in a preferred embodiment of the invention, TMR induces revascularization and angiogenesis in an ischemic cardiovascular region and, hence, damaged cardiovascular tissue, by generating a volumetric void or cavity therein via the transmission of light energy, e.g. a $CO_2$ laser energy.

The term "TMR event", as used herein, thus means and includes the transmission of external energy to a cardiovascular structure or tissue associated therewith via a TMR apparatus that induces revascularization and/or angiogenesis in the cardiovascular structure and, hence, tissue associated therewith.

As will be appreciated by one having ordinary skill in the art, a TMR event also induces a biological insult to cardiovascular tissue. Thus, for purposes herein, the term "TMR event" is also deemed a tissue inciting event.

According to the invention, TMR can be achieved via various TMR apparatus, including, without limitation, the devices described in U.S. Pat. Nos. 5,725,523, 5,738,680, 5,785,702, 5,807,384 and 6,042,581, which are incorporated by reference herein in their entirety. TMR can also be achieved via any device or method of inducing an inciting event.

The term "ventricular assistance," as used herein, means and includes any means of supporting and/or assisting the function of a heart or a parameter associated therewith. Ventricular assistance, as used herein, thus means and includes cardiovascular support and/or assistance via various means and apparatus, including, without limitation, a right ventricular assist device (RVAD), left ventricular assist device (LVAD), left and right ventricular assist device (BiVAD), pacemaker, biventricular pacemaker, implantable cardioverter defibrillator (ICD) and other mechanical circulatory support (MCS) devices.

The terms "delivery" and "administration" are used interchangeably herein, and mean and include providing a functional agent or formulation, e.g., an "ECM composition," "ECM based composition" and/or "pharmacological composition", or energy, e.g., laser energy, kinetic energy, and/or chemical energy, to a treatment site, e.g., damaged tissue and/or ischemic tissue, through any method appropriate to deliver the functional agent or formulation or energy to the treatment site. Non-limiting examples of formulation delivery methods include direct delivery or injection, percutaneous delivery and topical application at the treatment site.

The terms "concomitant" and "jointly" as used herein in connection with the administration of an ECM based composition of the invention and ventricular assistance, mean that the ECM based composition and ventricular assistance are administered (or provided) concurrently at a defined point in time, i.e. the administration of the ECM based composition and ventricular assistance occur together at a defined point in time.

The term "in conjunction with", as used herein in connection with the administration of an ECM based composition of the invention and ventricular assistance or an inciting event or a TMR event, mean that the ECM based composition and ventricular assistance or tissue inciting event or TMR event are administered (or provided) within a defined period of time of each other. As discussed in detail herein, in some embodiments of the invention, the ECM based composition and ventricular assistance and/or tissue inciting event and/or TMR event are administered (or provided) within a period of time less than 60 minutes of each other. In some embodiments, the ECM based composition and ventricular assistance and/or tissue inciting event and/or TMR event are administered (or provided) within a period of time less than 30 minutes of each other. In some embodiments, the ECM based composition and ventricular assistance and/or tissue inciting event and/or TMR event are administered (or provided) within a period of time less than 10 minutes of each other.

The term "percutaneous", as used herein, means and includes any penetration through the skin of a patient or subject, whether in the form of a small cut, incision, hole, cannula, tubular access sleeve or port or the like.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As indicated above, the present invention is directed to ECM based compositions and methods for treating damaged or diseased biological tissue.

In a preferred embodiment of the invention, the ECM based compositions include at least one decellularized or acellular ECM derived from a mammalian tissue source.

According to the invention, the ECM can be derived from various mammalian tissue sources and methods for preparing same, such as disclosed in U.S. Pat. Nos. 7,550,004, 7,244,444, 6,379,710, 6,358,284, 6,206,931, 5,733,337 and 4,902,508 and U.S. application Ser. No. 12/707,427; which are incorporated by reference herein in their entirety. The mammalian tissue sources include, without limitation, small intestine submucosa (SIS), urinary bladder submucosa (UBS), stomach submucosa (SS), central nervous system tissue, epithelium of mesodermal origin, i.e. mesothelial tissue, dermal tissue, subcutaneous tissue, gastrointestinal tissue, i.e. large and small intestine tissue, tissue surrounding growing bone, placental tissue, omentum tissue, cardiac tissue, e.g., pericardium and/or myocardium tissue, kidney tissue, pancreas tissue, lung tissue, and combinations thereof. The ECM can also comprise collagen from mammalian sources.

The ECM can also be derived from basement membrane of mammalian tissue/organs, including, without limitation, urinary basement membrane (UBM), liver basement membrane (LBM), and amnion, chorion, allograft pericardium, allograft acellular dermis, amniotic membrane, Wharton's jelly, and combinations thereof.

According to the invention, the improved ECM based compositions can comprise mixed liquids, mixed emulsions, mixed gels, mixed pastes, or mixed solid ECM particulates. The ECM based compositions can also comprise solid members, such as sheets or grafts.

According to the invention, the ECM particulates can be fluidized, as described in U.S. Pat. Nos. 5,275,826, 6,579, 538 and 6,933,326, to form a fluidized ECM based composition of the invention.

According to the invention, various conventional means can be employed to form a particulate ECM of the invention. In some embodiments, the ECM is formed into a sheet, fluidized (or hydrated), frozen and ground.

Preferably, the particulate ECM is subsequently filtered to achieve a desired particulate size. In some embodiments, the particulate ECM preferably has a particulate size no greater than 2000 microns. In some embodiments, the particulate ECM preferably has a particulate size no greater than 500 microns.

In a preferred embodiment, the particulate ECM has a particulate size in the range of approximately 20 microns to 300 microns.

As indicated above, according to the invention, the particulate ECM can be fluidized i.e. combined with a liquid or gel, to form a fluidized ECM based composition of the invention.

In some embodiments of the invention, the particulate ECM is combined with a suitable buffer solution, such as saline.

Preferably, the concentration of the buffer solution is in the range of about 0.001 mg/ml to about 200 mg/ml. Suitable concentration ranges thus include, without limitation, about 5 mg/ml to about 150 mg/ml, about 10 mg/ml to about 125 mg/ml, about 25 mg/ml to about 100 mg/ml, about 20 mg/ml to about 75 mg/ml, about 25 mg/ml to about 60 mg/ml, about 30 mg/ml to about 50 mg/ml, and about 35 mg/ml to about 45 mg/ml and about 40 mg/ml. to about 42 mg/ml.

The noted concentration ranges are, however, merely exemplary and not intended to be exhaustive or limiting. It is understood that any value within any of the listed ranges is deemed a reasonable and useful value for a concentration of a liquid or semi-solid component of an ECM of the invention.

According to the invention, the ECM based compositions of the invention can further include one or more of the biologically active or pharmacological agents disclosed in U.S. application Ser. No. 14/644,476 and/or referenced above (also referred to herein as "exogenously added" agents), which aid in the treatment of damaged tissue and/or facilitate bioremodeling and/or angiogenesis and/or tissue regeneration processes.

In some embodiments of the invention, the biologically active agent comprises one of the aforementioned growth factors, e.g., TGF-β, bFGF and VEGF.

In some embodiments of the invention, the biologically active agent comprises an exosome (referred to hereinafter "exosome augmented ECM based compositions").

As indicated above, exosomes comprise a lipid bilayer structure that contains or encapsulates a biologically active agent, such as a growth factor, e.g. TGF-β, TGF-α, VEGF and insulin-like growth factor (IGF-I), cytokine, e.g. interleukin-8 (IL-8), transcription factor and micro RNA (miRNA).

As is well established, exosomes significantly enhance the delivery of biologically active agents (and, as discussed below, encapsulated pharmacological agents) to cells through two seminal properties/capabilities. The first property comprises the capacity of exosomes to shield encapsulated agents (via the exosome lipid bilayer) from proteolytic agents, which can, and often will, degrade unshielded (or free) bioactive molecules and render the molecules non-functional in biological tissue environments.

The second property of exosomes comprises the capacity to directly and, hence, more efficiently deliver encapsulated agents; particularly, encapsulated biologically active agents, to endogenous cells in the biological tissue.

As is well known in the art, endogenous cells typically do not comprise the capacity to "directly" interact with "free" biologically active agents, such as growth factors. There must be additional biological processes initiated by the endogenous cells to interact directly with biologically active agents, e.g. expression of receptor proteins for or corresponding to the biologically active agents.

Exosomes facilitate direct interaction by and between endogenous cells and exosome encapsulated biologically active agents (and, hence, direct delivery of bioactive molecules to endogenous cells), which enhances the bioactivity of the agents.

According to the invention, when a naturally occurring endogenous exosome comprising an encapsulated growth factor comprising bFGF, TGF-β or VEGF is delivered to damaged cardiovascular tissue, the exosome induces neovascularization, stem cell proliferation, bioremodeling of the damaged tissue, and regeneration of new tissue and tissue structures.

According to the invention, when a naturally occurring endogenous exosome comprising an encapsulated growth factor comprising an inflammation modulating agent, such as a cytokine, e.g. interleukin-8 (IL-8), or a transcription factor and micro RNA (miRNA), is delivered to damaged cardiovascular tissue, the exosome modulates inflammation of the damaged tissue.

According to the invention, when an exosome augmented ECM based composition (i.e. an ECM based composition comprising acellular ECM and an exogenously added exosome) is delivered to the damaged cardiovascular tissue, the exosome augmented ECM based composition can, and in most instances will, induce and/or support a multitude of significant biological processes in vivo, including (i) inflammation modulation of the damaged tissue, (ii) neovascularization, (iii) stem cell proliferation, (iv) bioremodeling of the damaged tissue, and (v) regeneration of new tissue and tissue structures.

Indeed, it has been found that when an exosome augmented ECM based composition comprising an exosome encapsulated inflammation modulating agent, such as an interleukin, e.g. IL-8, or a miRNA, is delivered to the damaged cardiovascular tissue, the exosome augmented ECM based composition significantly enhances inflammation modulation of the damaged tissue. When the exosome augmented ECM based composition comprises an exosome encapsulated growth factor, such as bFGF or VEGF (alone or with an exosome encapsulated inflammation modulating agent) is delivered to the damaged cardiovascular tissue, the exosome augmented ECM based composition also significantly enhances neovascularization, stem cell proliferation, bioremodeling of the damaged tissue, and regeneration of new tissue and tissue structures, compared to neovascularization, stem cell proliferation, bioremodeling and regeneration of new tissue and tissue structures induced by acellular ECM alone.

By way of example, according to the invention, when an exosome augmented ECM based composition comprising exosome encapsulated IL-8 is disposed proximate damaged cardiovascular tissue, the exosome augmented ECM based composition modulates the transition of M1 type "acute inflammatory" macrophages to M2 type "wound healing" macrophages that is initiated by the acellular ECM.

By way of further example, when an exosome augmented ECM based composition comprising an exosome encapsulated miRNA, e.g. miR-210, miR-132, and miR-146a-3p, is delivered to the damaged cardiovascular tissue, the exosome augmented ECM based composition induces enhanced stem cell proliferation via the delivery of exosome encapsulated miRNAs and transcription factors to the damaged cardiovascular tissue, which signals the endogenous stem cells to bind and/or attach to the acellular ECM and proliferate.

When an exosome augmented ECM based composition comprising an encapsulated miRNA is delivered to the damaged cardiovascular tissue, the exosome augmented ECM based composition will also target and suppress seminal cytokines that promote apoptosis of functioning cells in damaged tissue.

In some embodiments, the exosomes are derived and, hence, processed from one of the aforementioned tissue sources, including, but not limited to, small intestine submucosa (SIS), urinary bladder submucosa (UBS), stomach submucosa (SS), central nervous system tissue, epithelium of mesodermal origin, i.e. mesothelial tissue, dermal tissue, subcutaneous tissue, gastrointestinal tissue, i.e. large and small intestine tissue, tissue surrounding growing bone, placental tissue, omentum tissue, cardiac tissue, e.g., pericardium and/or myocardium tissue, kidney tissue, pancreas tissue, lung tissue.

In some embodiments, the exosomes are processed and derived from a mammalian fluid composition, including, but not limited to, blood, amniotic fluid, lymphatic fluid, interstitial fluid, pleural fluid, peritoneal fluid, pericardial fluid and cerebrospinal fluid.

In some embodiments of the invention, the exosomes are derived from amniotic membrane, placenta or Whartons jelly.

In some embodiments, exosomes are derived and, hence, processed from an in vitro or in vivo cultured cell, including, but not limited to, one of the cells disclosed in U.S. application Ser. No. 14/644,476 and/or referenced herein.

In some embodiments, the exosomes are derived from mesenchymal stem cells (MSCs).

In some embodiments, the MSCs are cultured in a cell culture media under hypoxic conditions to induce a higher production rate of MSC-derived exosomes.

In some embodiments, the MSCs are cultured on acellular ECM. According to one aspect of the invention, the MSCs condition the acellular ECM by releasing exosomes and, thereby, form an exosome augmented ECM based composition of the invention.

According to the invention, the exosomes of the invention can be isolated from a mammalian bodily fluid or cell culture media using any known conventional method, such as ultra-centrifugation.

According to the invention, the exosomes can also be synthetically modified to alter the structure of the exosomes (referred to hereinafter as "synthetically modified exosomes").

In some embodiments of the invention, the exosomes are synthetically modified to enhance the effective concentration of the encapsulated biologically active agent, e.g. bFGF.

In some embodiments of the invention, the exosomes are synthetically modified to encapsulate a different biologically active agent.

In some embodiments of the invention, the exosomes are synthetically modified to encapsulate a pharmacological agent, e.g., cerivastatin.

According to the invention, the exosomes of the invention can be synthetically modified to encapsulate any of the biologically active agents and/or pharmacological active agents disclosed in U.S. application Ser. No. 14/644,476 and/or referenced herein.

Thus, in some embodiments of the invention, the exosomes are synthetically modified to encapsulate a growth factor, including, but not limited to bFGF, TGF-β and VEGF.

In some embodiments of the invention, the exosomes are synthetically modified to encapsulate a microRNA (miRNA) and/or fragments thereof including, without limitation, miR-23a, miR-23b, miR-24, miR-26a, miR27-a, miR-30c, let-7e, mir-19b, miR-125b, mir-27b, let-7a, miR-19a, let-7c, miR-140-3p, miR-125a-5p, miR-132, miR-150, miR-155, mir-210, let-7b, miR-24, miR-423-5p, miR-22, let-7f, miR-146a, miR-17, miR-21, miR-92, miR92a, miR-29, miR-29a, miR-29b, miR-29c, miR-34, mi-R34a, miR-150, miR-451, miR-145, miR-143, miR-144, miR-193a-3p, miR-133a, miR-155, miR-181a, miR-214, miR-199b, miR-199a, miR-210, miR-126, miR-378, miR-363, miR-30b, miR-499.

According to the invention, the synthetically modified exosomes similarly markedly improve the efficacy of biologically active agents and/or the pharmacological active agents by providing an efficient and highly effective means of traversing the cell membrane of endogenous cells.

According to the invention, the exosomes (including synthetically modified exosomes) can be suspended in a suitable buffer solution to form an exosome solution.

In some embodiments of the invention, the exosomes (including semi-synthetically modified exosomes) are suspended in a saline solution, such as phosphate buffered saline (PBS).

In some embodiments, the exosome solution preferably comprises an exosome concentration in the range of $1\text{-}9.0*10^{12}$ exosomes/ml.

As indicated above, when an exosome augmented ECM based composition is delivered to the damaged cardiovascular tissue, the exosome augmented ECM based composition significantly enhances inflammation modulation of the damaged tissue. The exosome augmented ECM based composition also significantly enhances neovascularization, stem cell proliferation, bioremodeling of the damaged tissue, and regeneration of new tissue and tissue structures, compared to neovascularization, stem cell proliferation, bioremodeling and regeneration of new tissue and tissue structures induced by acellular ECM alone.

Referring now to FIG. 1, there is shown a depiction of a normal human heart 100. The heart wall 102 consists of an inner layer of simple squamous epithelium, referred to as the endocardium. The endocardium overlays the myocardium (a variably thick heart muscle) and is enveloped within a multi-layer tissue structure referred to as the pericardium. The innermost layer of the pericardium, referred to as the visceral pericardium or epicardium, covers the myocardium. An outermost layer of the pericardium, referred to as the fibrous pericardium, attaches the parietal pericardium to the sternum, the great vessels and the diaphragm.

Figure 2:
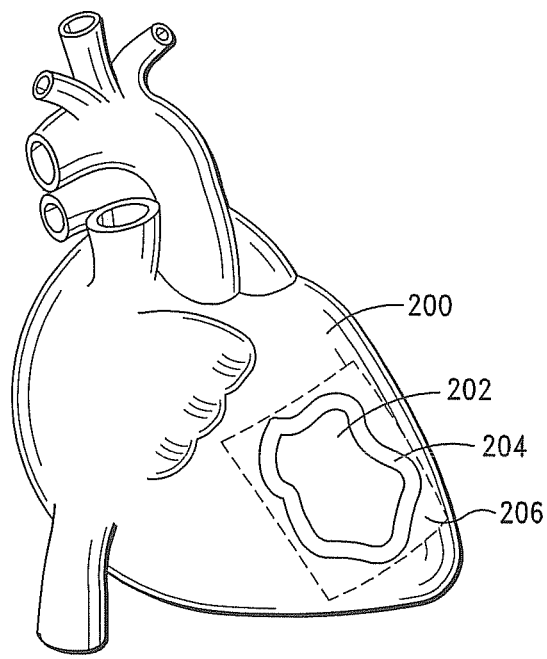
FIG. 2 is an illustration of a heart having an ischemic infarcted region.

Referring now to FIG. 2, there is shown a depiction of a heart 200 having an ischemic infarcted region 202 and a peri-infarcted region 204, which is surrounded by healthy non-ischemic myocardium tissue 206.

As indicated above, the ischemic infarcted region 202 (or myocardial infarction) can, and, in many instances, will trigger a cascading sequence of myocellular events. In many instances, the myocellular events lead to deterioration in ventricular function and heart failure.

According to the invention, an ischemic infarcted region and the effects thereof can be ameliorated or eliminated by delivering an ECM based composition and, in particular, an exosome augmented ECM based composition of the invention, directly to the infarcted cardiovascular tissue, which will induce neovascularization, host tissue proliferation, bioremodeling of tissue associated with the ischemic infarcted region, and regeneration of new cardiovascular tissue and structures with site-specific structural and functional properties.

According to the invention, the ECM based compositions can be delivered to an ischemic infarcted region (or peri-infarcted region) and, hence, infarcted cardiovascular tissue associated therewith, as well as other damaged or diseased biological tissue, by various conventional means, including direct injection, topical delivery and delivery via a prosthetic construct, e.g., graft.

In some embodiments, the ECM based compositions comprise and, hence, are delivered to target tissue, e.g., infarcted cardiovascular tissue by a prosthetic construct, such as disclosed in U.S. application Ser. No. 15/386,610, which is incorporated by reference herein in its entirety.

Figure 4:
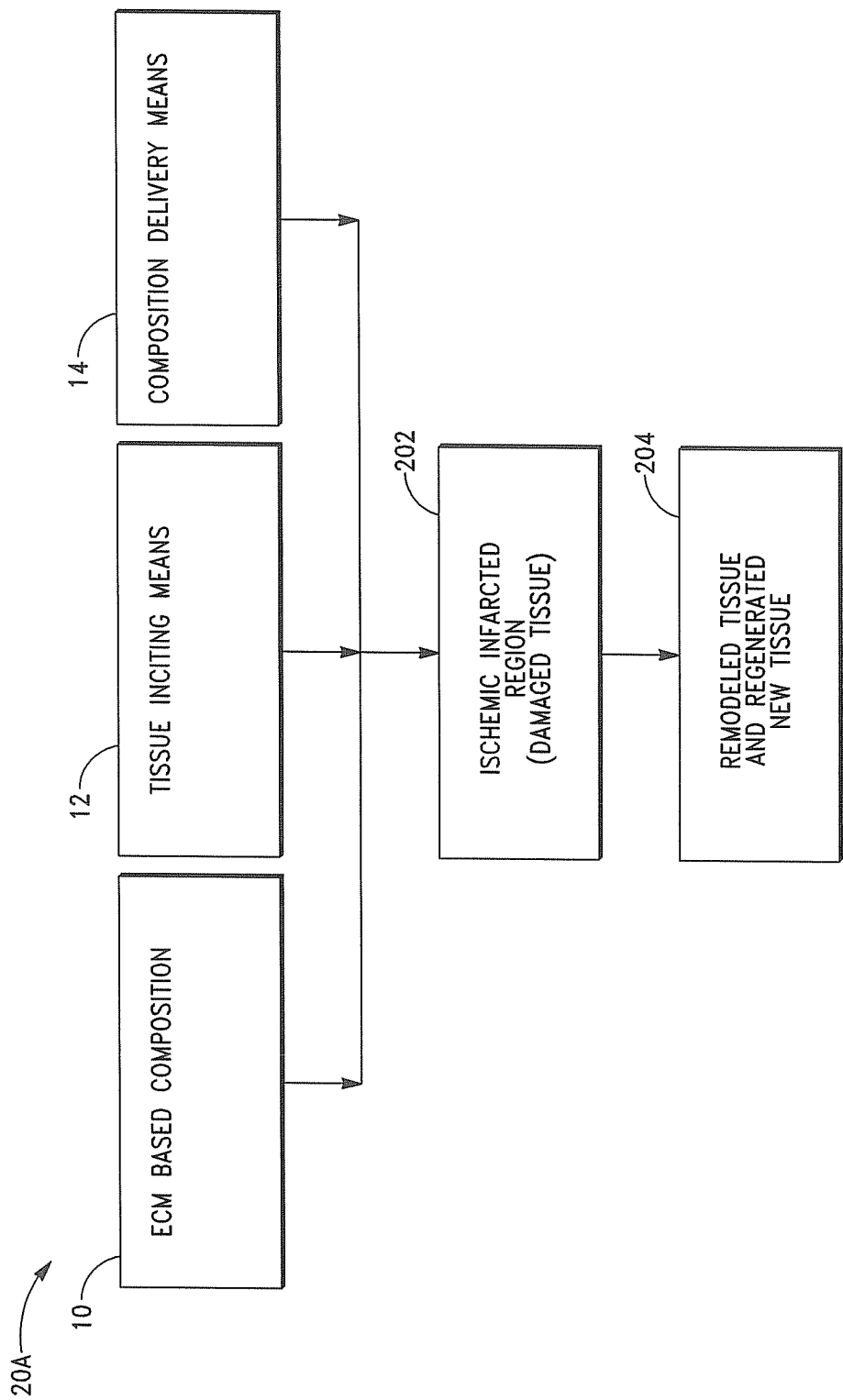
FIG. 4 is a schematic illustration of one embodiment of a method for delivering an ECM based composition of the invention to an ischemic infarcted region, in accordance with the invention.

Referring now to FIG. 4, there is shown an illustration of one embodiment of an ECM based composition delivery method of the invention. As illustrated in FIG. 4, the delivery method (denoted "20A") comprises the provision and use of an ECM based composition 10 and composition delivery means 14.

In some embodiments, the composition delivery means 14 comprises a multi-needle injection system, such as disclosed in U.S. application Ser. No. 14/031,630, filed on Sep. 19, 2013, and illustrated in FIGS. 3A and 3B.

As illustrated in FIG. 4, in a preferred embodiment of the invention, the ECM based composition 10 is delivered (or administered) to a ischemic infarcted region 202 and, hence, infarcted cardiovascular tissue associated therewith.

According to the invention, the ECM based composition 10 can also be delivered to a peri-infarcted region 204, and, hence, infarcted tissue associated therewith, and non-infarcted tissue.

As illustrated in FIG. 4, in some embodiments of the invention, the delivery method 20A further comprises tissue inciting means 12. In a preferred embodiment of the invention, the tissue inciting means 12 is adapted to induce a biological insult or tissue damage and, thereby, cellular migration and/or a release of cytokines, including growth factors and/or other bioactive molecules, and/or other cellular activities that are associated with inflammation modulation and/or stem cell proliferation and/or neovascularization.

Thus, according to the invention, the tissue inciting means 12 can comprise various methods and apparatus to induce a biological insult or tissue damage, including, without limitation, mechanical means, pneumatic means, radiation emitting means, chemical means and biological means.

In a preferred embodiment of the invention, the tissue inciting means 12 is administered proximate the composition delivery region(s), i.e. the tissue regions receiving the ECM based composition(s) 10 delivered via the composition delivery means 14.

Preferably, the tissue inciting means 12 is administered to the ischemic infarcted region 202 (or peri-infarcted region) and, hence, infarcted cardiovascular tissue associated therewith.

In some embodiments, the tissue inciting means 12 comprises piercing or perforating the ischemic infarcted region and, hence, damaged cardiovascular tissue associated therewith.

In embodiments where the composition delivery means 14 comprises a needle-based injection system, such as the multi-needle injection apparatus disclosed in U.S. application Ser. No. 14/031,630 and illustrated in FIGS. 3A and 3B or the needle-based injection system disclosed in U.S. Pat. No. 9,539,410, the tissue inciting means 12 comprises (or is provided by) the needles of the device, which are adapted to pierce the damaged cardiovascular tissue.

In a preferred embodiment of the invention, the tissue inciting means 12 is administered in conjunction with the administration of the ECM based composition 10 by the composition delivery means 14.

In some embodiments of the invention, the ECM based composition 10 and tissue inciting event 12 are administered (or provided) within a period of time less than 10 minutes of each other.

In some embodiments, the ECM based composition 10 is administered within a period of time of approximately 10-240 minutes after administering (or providing) the tissue inciting event 12.

As further illustrated in FIG. 4 and discussed in detail above, when the ECM based ECM composition 10 is delivered to an ischemic infarcted region 202 (or a peri-infarcted region 204) and, hence, damaged cardiovascular tissue associated therewith, the damaged cardiovascular tissue is remodeled and new cardiovascular tissue is regenerated 204.

Figure 5:
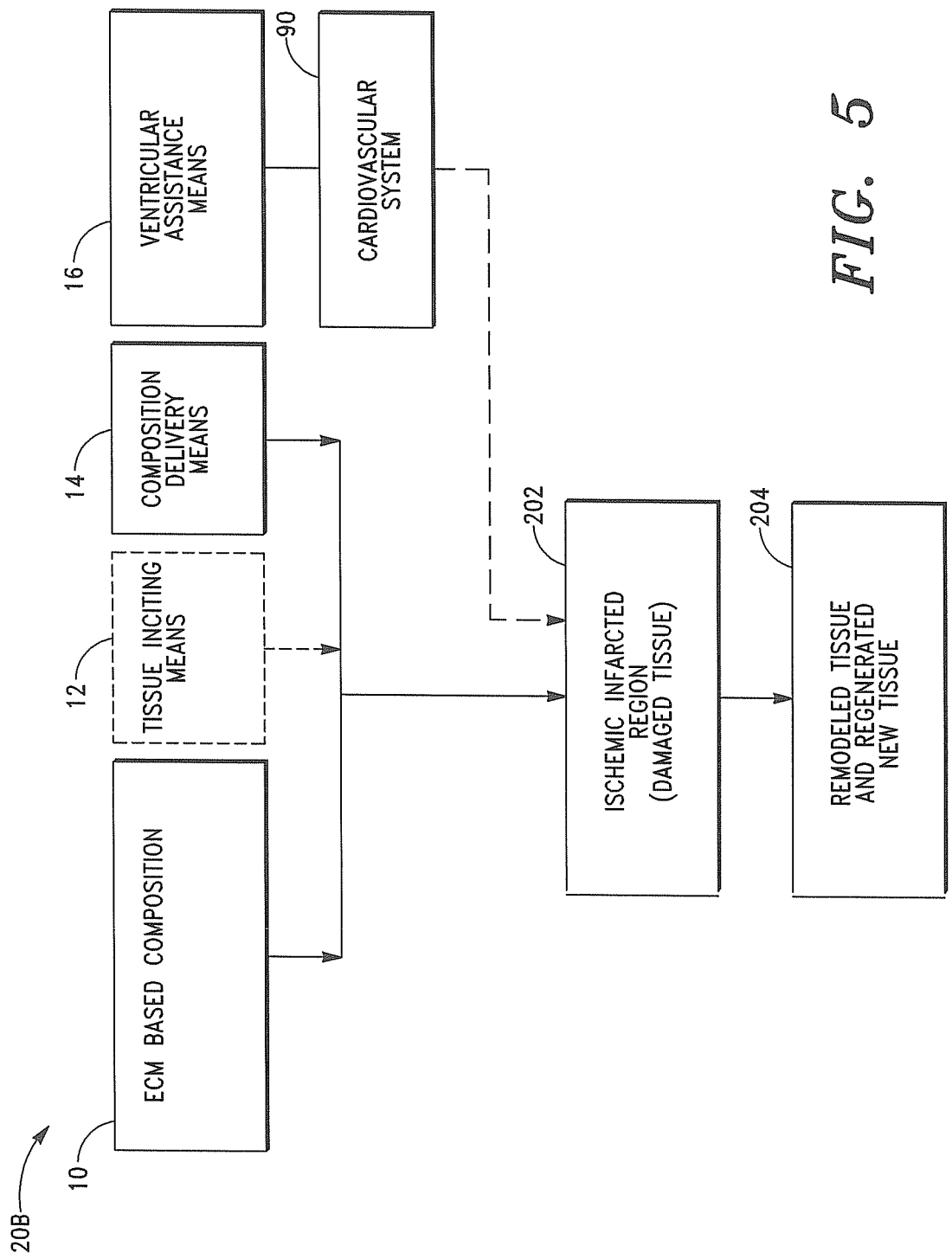
FIG. 5 is a schematic illustration of one embodiment of a method for delivering an ECM based composition of the invention to an ischemic infarcted region in conjunction with ventricular assistance, in accordance with the invention.

Referring now to FIG. 5, there is shown an illustration of another embodiment of an ECM based composition delivery method of the invention. As illustrated in FIG. 5, the delivery method (denoted "20B") similarly comprises the provision and use of an ECM based composition 10 and composition delivery means 14. However, in this embodiment, the delivery method 20B further comprises the provision and use of ventricular assistance means 16, such as discussed in detail in U.S. Pat. Nos. 9,119,899, 8,871,511, 9,161,952, 9,265,798, 9,265,799 and 9,327,000, which are expressly incorporated by reference herein (referred to hereinafter as "VAD assisted delivery method").

According to the invention, the composition delivery means 14 can similarly comprise direct injection, topical delivery and delivery via a prosthetic construct, e.g., graft.

In some embodiments of the invention, the composition delivery means 14 similarly comprises a needle-based injection apparatus, such as the multi-needle injection apparatus illustrated in FIGS. 3A and 3B.

As illustrated in FIG. 5, in a preferred embodiment of the invention, the ECM based composition 10 is similarly delivered (or administered) to a ischemic infarcted region 202 and, hence, infarcted cardiovascular tissue associated therewith.

According to the invention, the ECM based composition 10 can also be delivered to a peri-infarcted region 204, and, hence, infarcted tissue associated therewith, and non-infarcted tissue.

As discussed in detail above, the ventricular assistance means 14 is adapted to support (or augment) the function of the cardiovascular system, e.g. circulatory system.

According to the invention, the ventricular assistance means 14 can thus comprise any of the aforementioned ventricular assist devices, such as a right ventricular assist device (RVAD) or left ventricular assist device (LVAD).

As illustrated in FIG. 5, in some embodiments of the invention, the VAD assisted delivery method 20B further comprises tissue inciting means 12. According to the invention, the tissue inciting means 12 can similarly comprise any of the aforementioned methods and apparatus, including, without limitation, mechanical means, pneumatic means, radiation emitting means, chemical means and biological means.

In a preferred embodiment of the invention, the tissue inciting means 12 is similarly administered proximate the composition delivery region(s), i.e. the tissue regions receiving the ECM based composition(s) 10 delivered via the composition delivery means 14.

Preferably, the tissue inciting means 12 is similarly administered to an ischemic infarcted region 202 (or a peri-infarcted region 204) and, hence, infarcted cardiovascular tissue associated therewith.

In a preferred embodiment of the invention, the ECM based composition 10 and ventricular assistance means 16 are administered (or provided) jointly at a defined point in time, i.e. the administration of the ECM based composition 10 and ventricular assistance means 16 occur together at a defined point in time.

In embodiments of the invention, wherein the delivery method 20B comprises tissue inciting means 12, the ventricular assistance means 16 and tissue inciting means 12 are preferably administered (or provided) in conjunction with the administration of the ECM based composition 10, i.e. the ventricular assistance means 16, tissue inciting means 12 and ECM based composition 10 are administered (or provided) within a defined period of time of each other.

In some embodiments of the invention, the ECM based composition 10 is administered to an ischemic infarcted region 202 (or a peri-infarcted region 204) and, hence, infarcted cardiovascular tissue associated therewith, and the ventricular assistance means 16 and tissue inciting means 12 are preferably administered (or provided) within a period of time in the range of approximately 5-60 minutes of each other.

As further illustrated in FIG. 5, when the ECM based ECM composition 10 is delivered to an ischemic infarcted region 202 (or a peri-infarcted region 204) and, hence, damaged cardiovascular tissue associated therewith, in conjunction with the provision of ventricular assistance means 16, and, if employed, tissue inciting means, the damaged cardiovascular tissue is similarly remodeled and new cardiovascular tissue is regenerated 204.

Figure 6:
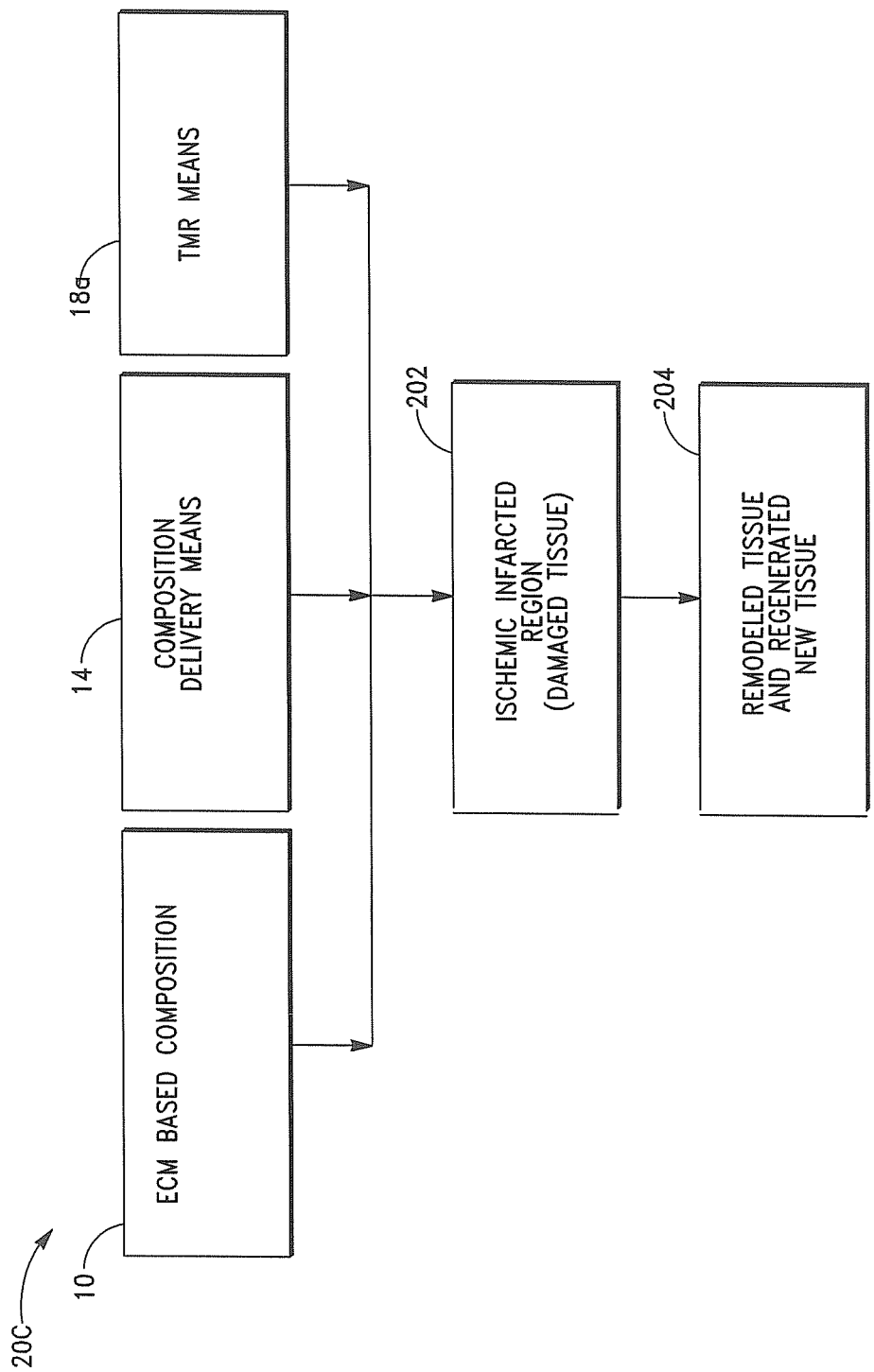
FIG. 6 is a schematic illustration of one embodiment of a method for delivering an ECM based composition of the invention to an ischemic infarcted region in conjunction with induced transmyocardial revascularization (TMR), in accordance with the invention.

Referring now to FIG. 6, there is shown an illustration of another embodiment of an ECM based composition delivery method of the invention. As illustrated in FIG. 6, the delivery method (denoted "20C") similarly comprises the provision and use of an ECM based composition 10 and composition delivery means 14. However, in this embodiment, the delivery method 20C further comprises the provision and use of transmyocardial revascularization (TMR) means 18a (referred to hereinafter as "TMR delivery method").

According to the invention, the TMR delivery method 20C can further include ventricular assistance means, such as a RVAD or LVAD.

According to the invention, the composition delivery means 14 can similarly comprise direct injection, topical delivery and delivery via a prosthetic construct, e.g., graft.

In some embodiments of the invention, the composition delivery means 14 similarly comprises a needle-based injection apparatus or system, such as the multi-needle injection apparatus illustrated in FIGS. 3A and 3B.

As illustrated in FIG. 6, in a preferred embodiment of the invention, the ECM based composition 10 is similarly delivered (or administered) to an ischemic infarcted region 202 and, hence, infarcted cardiovascular tissue associated therewith.

According to the invention, the ECM based composition 10 can also be delivered to a peri-infarcted region 204, and, hence, infarcted tissue associated therewith, and non-infarcted tissue.

As further illustrated in FIG. 6, in a preferred embodiment of the invention, the TMR means 18a is similarly administered (or provided) to an ischemic infarcted region 202 and, hence, infarcted cardiovascular tissue associated therewith.

According to the invention, the TMR means 18a can also be administered (or provided) to a peri-infarcted region 204, and, hence, infarcted tissue associated therewith, and non-infarcted tissue.

Figure 8:
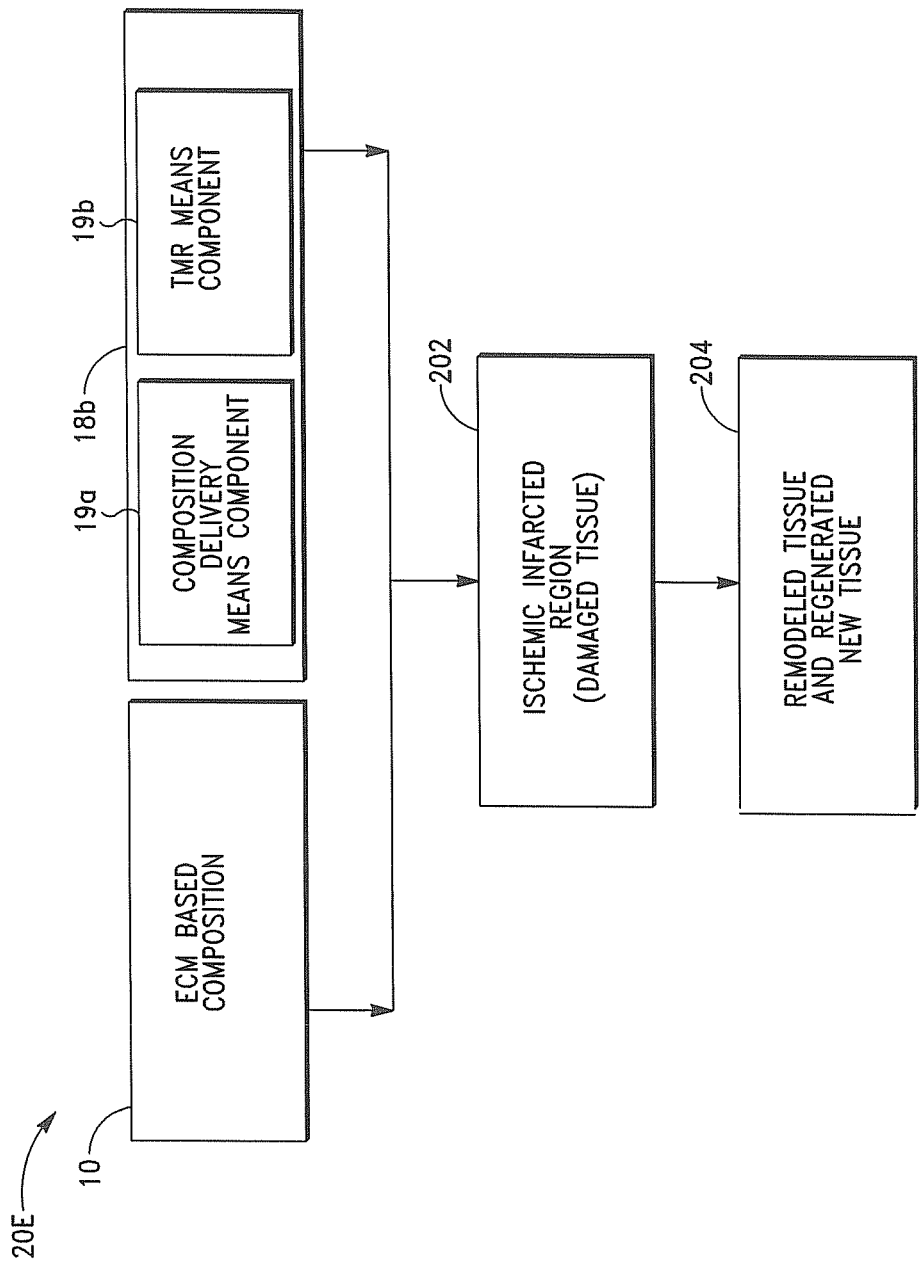
FIG. 8 is a schematic illustration of yet another embodiment of a method for delivering an ECM based composition of the invention to an ischemic infarcted region in conjunction with induced transmyocardial revascularization (TMR), in accordance with the invention.

As discussed in detail above, the TMR means 18a (and TMR component 19b of joint TMR/composition delivery system 18b shown in FIG. 8) is adapted to induce revascularization and/or angiogenesis in a cardiovascular structure; particularly, an ischemic infarcted region 202 (or a peri-infarcted region 204) of the structure and, hence, cardiovascular tissue associated therewith, by transmitting external energy to the cardiovascular structure or tissue, wherein the tissue structure is disrupted and, in at least one aspect, a volumetric void or cavity is generated in the cardiovascular structure.

According to the invention, the TMR means 18a can comprise various conventional TMR devices, including, without limitation, the TMR devices disclosed in U.S. Pat. Nos. 5,725,523, 5,738,680, 5,785,702, 5,807,384, 6,042,581, which are expressly incorporated by reference herein in their entirety.

In some embodiments of the invention, the TMR device comprises the device disclosed in U.S. Pat. No. 5,738,680.

Figure 9:
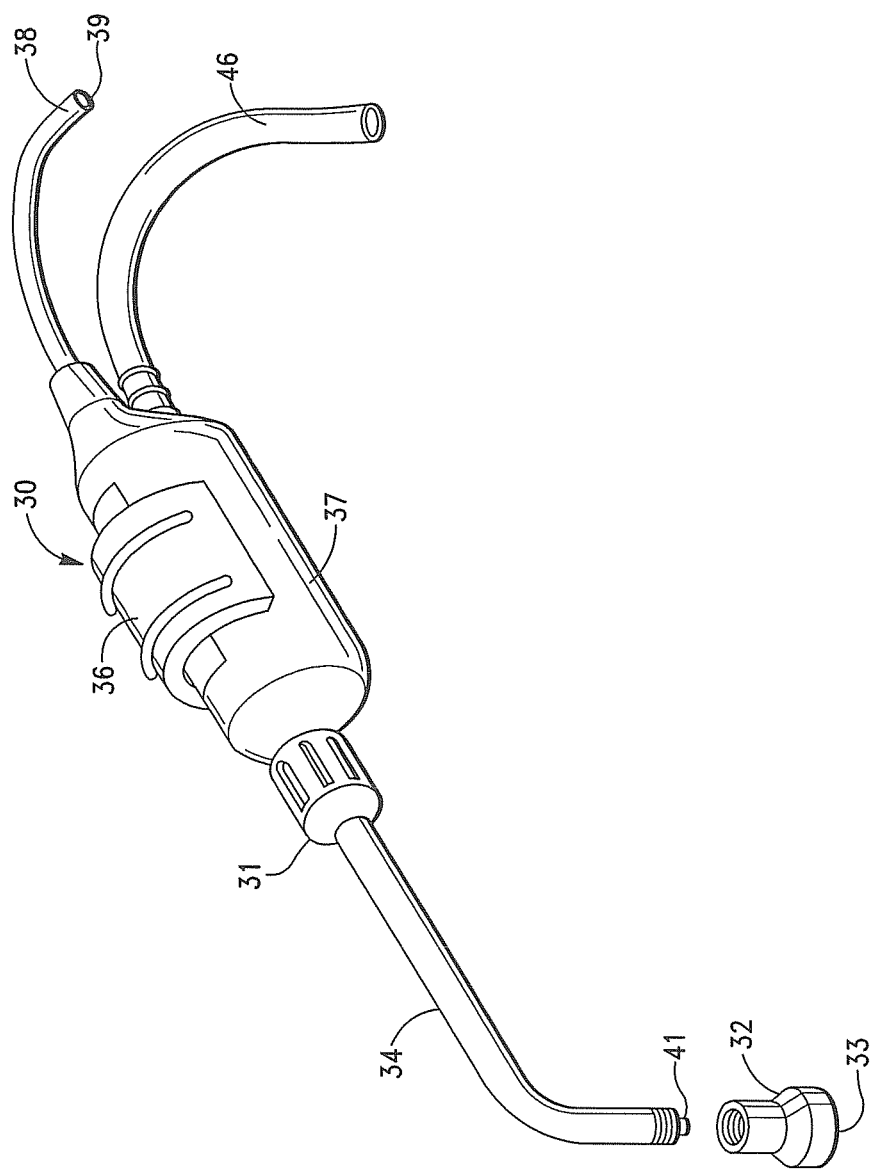
FIG. 9 is a perspective illustration of a prior art TMR apparatus.
Figure 10:
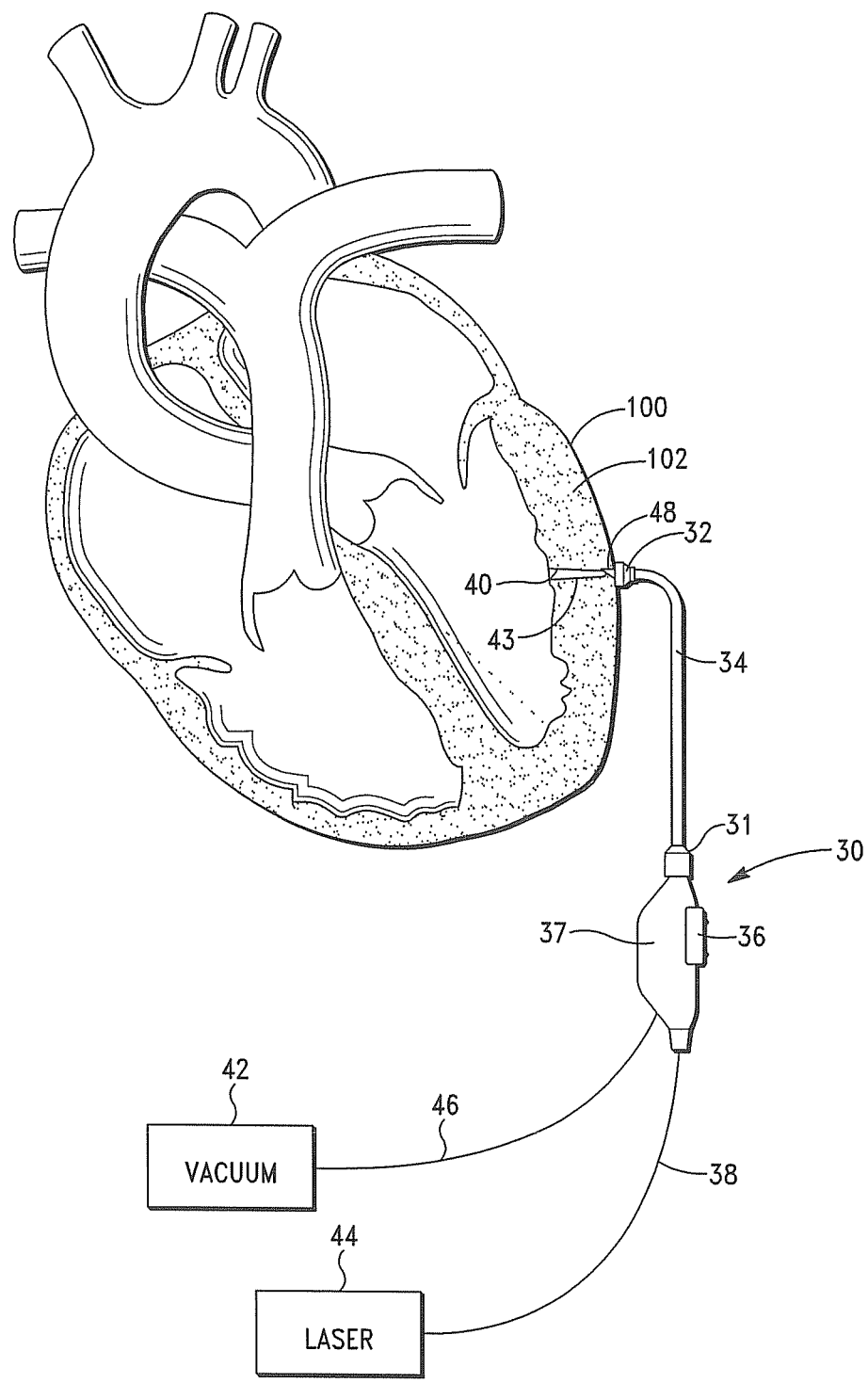
FIG. 10 is an illustration of the TMR apparatus shown in FIG. 9 engaged to a myocardium.
Figure 12:
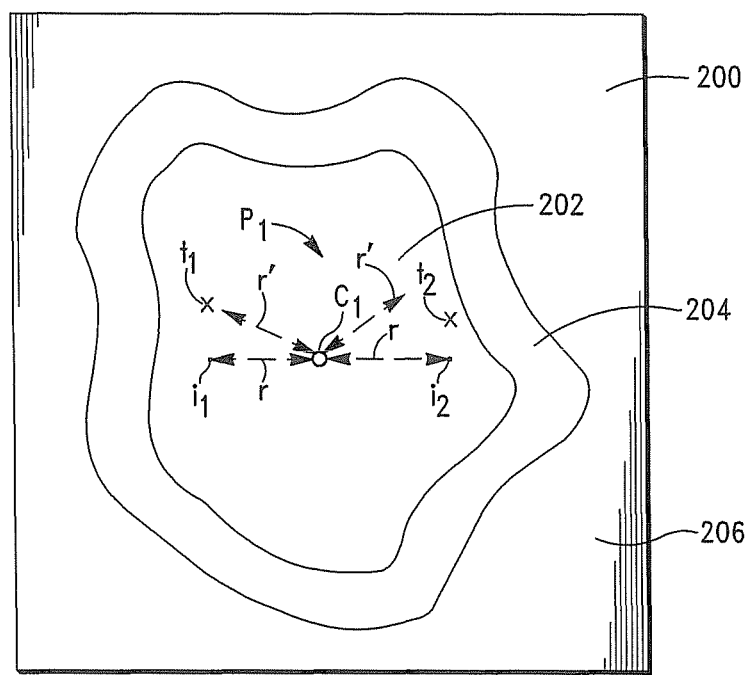
FIG. 12 is an illustration of an ischemic infarcted region of a heart with one embodiment of a TMR/incited tissue/composition delivery pattern, in accordance with the invention.

As illustrated in FIGS. 9 and 10, the noted TMR device 30 comprises a housing 37 adapted to be hand-held by an operator, e.g. surgeon, during an operative procedure, a "J-shaped" tubular member 34 that is in direct communication with the housing 37 at a proximal neck member 31 and an interchangeable distal head member 32 having a hollow piercing tip 48 (shown in FIG. 12).

The TMR device 30 further comprises an optical fiber bundle 38, comprising a proximal end 39 that is connected to a laser source 44 and extends through the housing 37 and tubular member 34 to the distal head member 32. Within the housing 37, the fiber bundle 38 is connected to a movable actuator (not shown) that extends outside the housing 37 and is in direct communication with a thumb-actuated control member 36. Movement of the control member 36 by a surgeon moves the distal end 41 of the fiber bundle 38 beyond the distal head member 32 of the tubular member 34.

The TMR device 30 further comprises a vacuum line 46 that is operatively connected to and extending from a vacuum source 42, such as a conventional hospital compressor. The vacuum line 46 is also connected to a housing inlet (not shown). The housing inlet communicates with an air passage around the fiber bundle 38 that extends through the tubular member 34 to distal head member 32. Thus, when the device 30 is employed during a surgical procedure, a vacuum force is provided at the distal head member 32 of the device 30.

As illustrated in FIG. 10, the vacuum force provided at the distal head member 32 draws myocardial tissue and, hence, myocardium 102 of a mammalian heart 100 firmly against the contacting face 33 of the distal head member 32. When the contacting face 33 of the distal head member 32 is positioned firmly against the myocardium 102, the hollow piercing tip 48 generates an initial opening in the myocardium 102 to allow the distal end 41 of the fiber bundle 38 to be routed through the hollow piercing tip 48 and engage the myocardium 102. As the fiber bundle 38 is advanced by the surgeon into the myocardium 102, laser pulses are emitted from the fiber bundle distal end 41 to form an energy impact region 40 and opening 43 through the myocardium 102.

As the fiber bundle 38 continues to advance, the vacuum force provided by the device 30 (i) removes biological debris produced by the laser and (ii) draws blood into the energy impact region 40 to initiate the revascularization process.

After the energy impact region 40 is formed, the fiber bundle 38 is retracted and the distal end member 32 is disengaged from the myocardium 102. Thereafter, the opening 43 in the energy impact region 40 seals by virtue of the natural clotting action of the blood in the impact region 40.

According to the invention, the ECM based composition 10 and TMR means 18a can be administered (or provided) to any location on mammalian heart 100. In some embodiments of the invention, the ECM based composition 10 and TMR means 18a are administered proximate or, as illustrated in FIG. 6, directly to an ischemic infarcted region 202.

In some embodiments of the invention, the ECM based composition 10 and TMR means 18a are administered proximate a peri-infarcted region 204.

In some embodiments of the invention, the ECM based composition 10 and TMR means 18a are administered to non-infarcted tissue.

In some embodiments of the invention, the TMR means 18a is administered (or provided to an ischemic infarcted region 202 (or a peri-infarcted region 204) jointly with the delivery or administration of the ECM based composition 10 to ischemic infarcted region 202 (or peri-infarcted region 204).

In some embodiments of the invention, the TMR means 18*a* is administered (or provided to an ischemic infarcted region 202 (or a peri-infarcted region 204) in conjunction with the delivery or administration of the ECM based composition 10 to ischemic infarcted region 202 (or peri-infarcted region 204).

In a preferred embodiment of the invention, the ECM based composition 10 and TMR means 18*a* are preferably administered (or provided) to an ischemic infarcted region 202 (or peri-infarcted region 204) and, hence, infarcted cardiovascular tissue associated therewith within a period of time less than twenty-four (24) hours, more preferably, sixty (60) minutes of each other.

Figure 11:
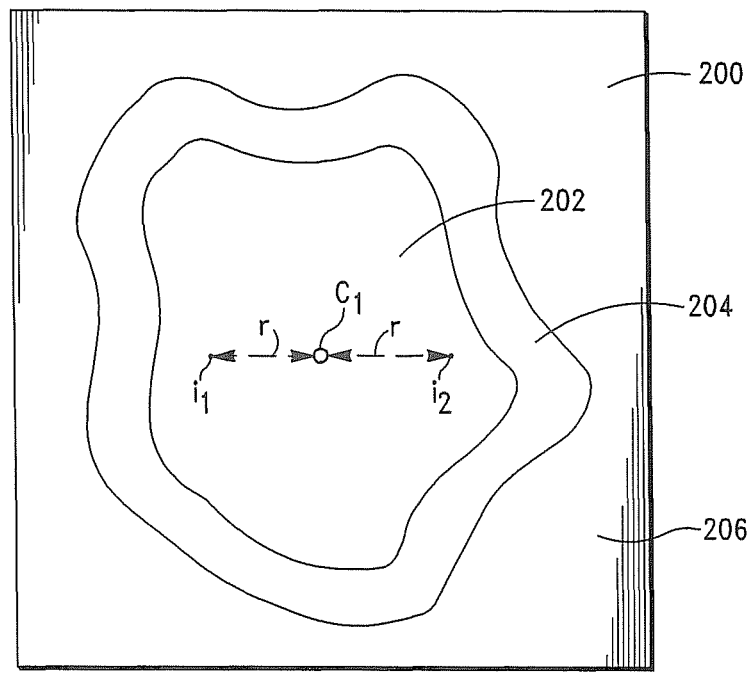
FIG. 11 is an illustration of an ischemic infarcted region of a heart with one embodiment of a TMR/composition delivery pattern, in accordance with the invention.

Referring now to FIG. 11, there is shown an ischemic infarcted region 202 that comprises a TMR impact region $C_1$ (i.e. a tissue region subjected to energy transmitted by the TMR means 18*a* and 18*b*, discussed below) and composition delivery regions $i_1$, $i_2$ (i.e. tissue regions that receive the ECM based composition 10 delivered by the composition delivery means 14), according to one embodiment of the invention.

As illustrated in FIG. 11, the composition delivery regions $i_1$, $i_2$ are preferably disposed at a distance "r" from the TMR energy impact region $C_1$.

As further illustrated in FIG. 11, the ECM based composition 10 is preferably delivered to the ischemic infarcted region 202 and, hence, cardiovascular tissue associated therewith.

As indicated above, the ECM based composition 10 can also be delivered to a peri-infarcted region 204 and, hence, cardiovascular tissue associated therewith, and tissue disposed proximate the peri-infarcted region 204.

In a preferred embodiment, the ECM based composition 10 is delivered to target tissue, such as infarcted tissue associated with an ischemic infarcted region 202 or a peri-infarcted region 204, no greater than a distance of 30 mm from a TMR impact region, i.e. r=≤30 mm.

In some embodiments of the invention, the ECM based composition 10 is delivered to target tissue, such as infarcted tissue associated with an ischemic infarcted region 202 or a per-infarcted region 204, within a distance of approximately 1-30 mm from a TMR impact region, i.e. r=1-30 mm.

According to the invention, there can be any number of composition delivery regions $i_1$, $i_2$, $i_3$, etc., and TMR impact regions $C_1$, $C_2$, $C_3$, etc.

In a preferred embodiment, at least one composition delivery region ($i_1$) is generated or provided (via the composition delivery means 14) proximate a TMR impact region ($C_1$).

In some embodiments, a plurality of composition delivery regions ($i_1$, $i_2$, $i_3$, etc.) is generated or provided proximate a TMR impact region ($C_1$). In some embodiments, the composition delivery regions ($i_1$, $i_2$, $i_3$, etc.) are disposed equidistant from the TMR impact region ($C_1$). In some embodiments, the composition delivery regions ($i_1$, $i_2$, $i_3$, etc.) are disposed at varying distances r from the TMR impact region ($C_1$).

Figure 7:
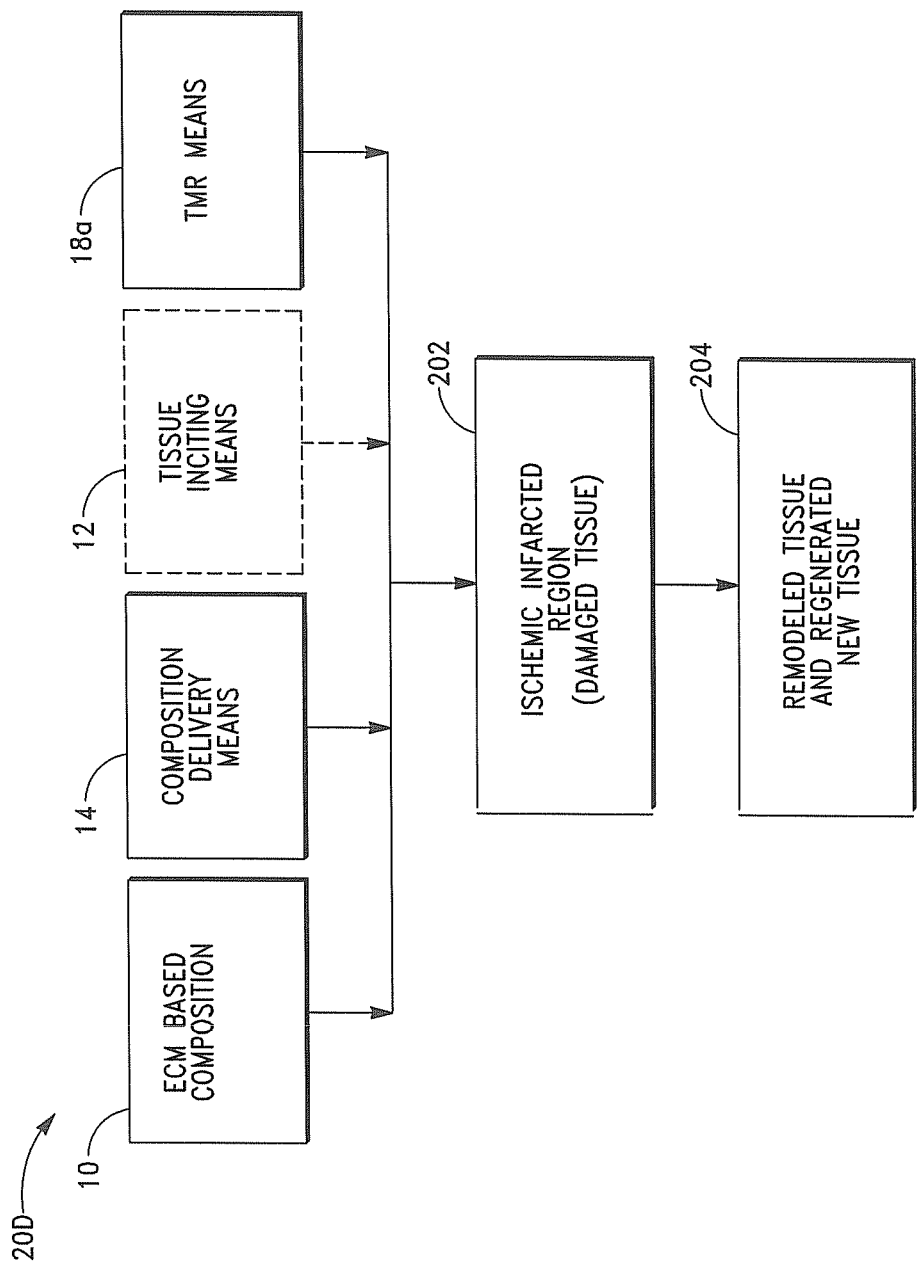
FIG. 7 is a schematic illustration of another embodiment of a method for delivering an ECM based composition of the invention to an ischemic infarcted region in conjunction with induced transmyocardial revascularization (TMR), in accordance with the invention.

Referring now to FIG. 7, there is shown another embodiment of a TMR delivery method of the invention (denoted "20D"). As illustrated in FIG. 7, the TMR delivery method 20D similarly comprises the provision and use of an ECM based composition 10, composition delivery means 14 and TMR means 18*a*. However, in this embodiment, the TMR delivery method 20D further comprises tissue inciting means 12.

According to the invention, the TMR delivery method 20D can similarly further include ventricular assistance means, such as a RVAD or LVAD.

According to the invention, the composition delivery means 14 can similarly comprise direct injection, topical delivery and delivery via a prosthetic construct, e.g., graft.

In some embodiments of the invention, the composition delivery means 14 similarly comprises a needle-based injection apparatus or system, such as the multi-needle injection apparatus illustrated in FIGS. 3A and 3B.

As illustrated in FIG. 7, in a preferred embodiment of the invention, the ECM based composition 10 is similarly delivered (or administered) to an ischemic infarcted region 202 and, hence, infarcted cardiovascular tissue associated therewith.

According to the invention, the ECM based composition 10 can also be delivered to a peri-infarcted region 204, and, hence, infarcted tissue associated therewith, and non-infarcted tissue.

According to the invention, the tissue inciting means 12 can similarly comprise any of the aforementioned methods and apparatus, including, without limitation, mechanical means, pneumatic means, radiation emitting means, chemical means and biological means.

In some embodiments of the invention, where the composition delivery means 14 comprises a needle-based apparatus, such as the apparatus illustrated in FIGS. 3A and 3B, by virtue of the pierced tissue by the needle(s) of the composition delivery means 14 and energy transmitted by the TMR means, the composition delivery means 14 and TMR means 18*a* both function as tissue inciting means 12, i.e. the composition delivery means 14 and TMR means 18*a* both provide a biological insult.

In embodiments of the invention where the composition delivery means 14 comprises a needleless pneumatic injector, by virtue of the high-pressure delivery of the ECM based composition 10 to the target tissue by the composition delivery means 14, both the composition delivery means 14 and TMR means 18*a* similarly function as tissue inciting means 12.

In a preferred embodiment of the invention, the tissue inciting means 12 is administered proximate the composition delivery region(s), i.e. the tissue regions receiving the ECM based composition(s) 10 delivered via the composition delivery means 14.

Preferably, the tissue inciting means 12 is administered to an ischemic infarcted region 202 (or a peri-infarcted region 204) and, hence, infarcted cardiovascular tissue associated therewith.

As illustrated in FIGS. 7 and 12, in a preferred embodiment of the invention, the ECM based composition 10 and tissue inciting means 12 are delivered to an ischemic infarcted region 202 and, hence, cardiovascular tissue associated therewith.

According to the invention, the ECM based composition 10 and tissue inciting means 12 can also be delivered to a peri-infarcted region 204 and, hence, cardiovascular tissue associated therewith, and tissue disposed proximate the peri-infarcted region 204.

In a preferred embodiment of the invention, the ECM based composition 10, tissue inciting means 12 and TMR means 18*a* are administered (or provided) to an ischemic infarcted region 202 and, hence, infarcted cardiovascular tissue associated therewith within a period of time less than 30 minutes of each other.

In a preferred embodiment, the ECM based composition 10 and tissue inciting means 12 are similarly delivered to target tissue, such as infarcted tissue associated with an ischemic infarcted region 202 or a per-infarcted region 204, no greater than a distance of approximately 30 mm from a TMR impact region, i.e. r=≤30 mm, as illustrated in FIG. 12.

In some embodiments of the invention, the ECM based composition 10 and tissue inciting means 12 are delivered to target tissue, such as infarcted tissue associated with the ischemic infarcted region 202 or peri-infarcted region 204, within a distance of approximately 1-30 mm from a TMR impact region, i.e. r=1-30 min.

According to the invention, any number of composition delivery regions $i_1$, $i_2$, $i_3$, etc., and incited tissue regions (denoted "$t_n$" in FIG. 12) and TMR impact regions $C_1$, $C_2$, $C_3$, etc. can similarly be generated or provided.

In a preferred embodiment, at least one composition delivery region ($i_1$) and incited tissue region $t_1$ are generated or provided proximate a TMR impact region ($C_1$).

In some embodiments, a plurality of composition delivery regions ($i_1$, $i_2$, $i_3$, etc.) and incited tissue regions ($t_1$, $t_2$, $t_3$, etc.) are similarly generated or provided proximate a TMR impact region ($C_1$). In some embodiments, the composition delivery regions ($i_1$, $i_2$, $i_3$, etc.) and incited tissue regions ($t_1$, $t_2$, $t_3$, etc.) are disposed equidistant from the TMR impact region ($C_1$). In some embodiments, the composition delivery regions ($i_1$, $i_2$, $i_3$, etc.) and incited tissue regions ($t_1$, $t_2$, $t_3$, etc.) are disposed at varying distances r and r' from the TMR impact region ($C_1$).

As indicated above, any number of composition delivery regions ($i_1$, $i_2$, $i_3$, etc.), incited tissue regions ($t_1$, $t_2$, $t_3$, etc.) and TMR impact regions ($C_1$, $C_2$, $C_3$, etc.) can similarly be generated or provided.

According to the invention, the composition delivery regions ($i_1$, $i_2$, $i_3$, etc.), incited tissue regions ($t_1$, $t_2$, $t_3$, etc.) and TMR impact regions ($C_1$, $C_2$, $C_3$, etc.) can also comprise various patterns. Illustrative are the composition delivery/incited tissue/TMR impact region patterns shown in FIGS. 12-15.

Referring first to FIG. 12, there is shown an ischemic infarcted region 202 having a composition delivery/incited tissue/TMR impact region pattern (denoted "$P_1$") comprising a TMR impact region $C_1$, incited tissue regions $t_1$, $t_2$ and composition delivery regions $i_1$, $i_2$, according to one embodiment of the invention.

As illustrated in FIG. 12, the composition delivery regions $i_1$, $i_2$ are disposed at a distance r from the TMR energy impact region $C_1$ and incited tissue regions $t_1$, $t_2$ are disposed at a distance r' from the TMR impact region $C_1$.

Figure 13:
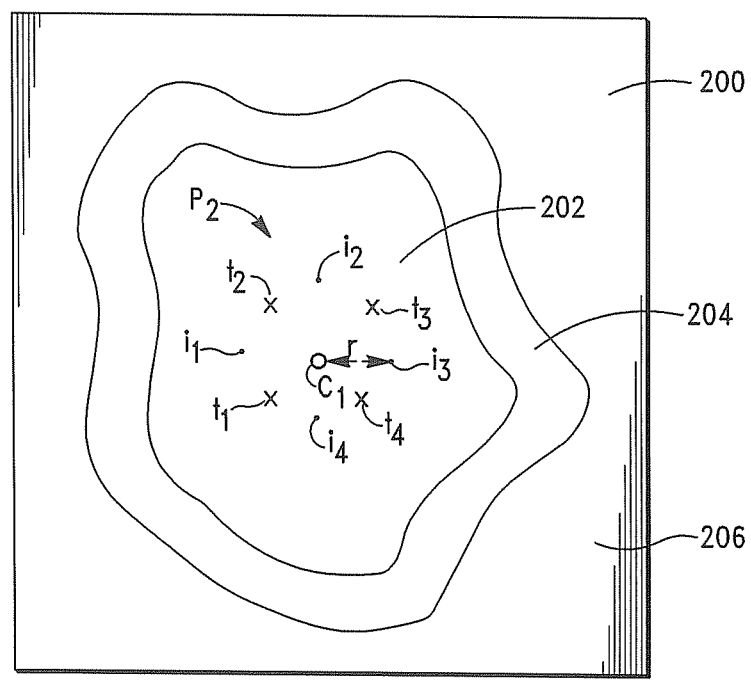
FIG. 13 is an illustration of an ischemic infarcted region of a heart with another embodiment of a TMR/incited tissue/composition delivery pattern, in accordance with the invention.

Referring now to FIG. 13, there is shown an ischemic infarcted region 202 having a composition delivery/incited tissue/TMR impact region pattern (denoted "$P_2$") comprising a TMR impact region $C_1$ and a radial arrangement of four (4) composition delivery regions $i_2$, $i_3$, $i_4$) and four (4) incited tissue regions ($t_1$, $t_2$, $t_3$, $t_4$), according to another embodiment of the invention.

As illustrated in FIG. 13, the composition delivery regions ($i_1$, $i_2$, $i_3$, $i_4$) and incited tissue regions ($t_1$, $t_2$, $t_3$, $t_4$) are disposed substantially equally spaced in the ischemic infarcted region 202.

Figure 14:
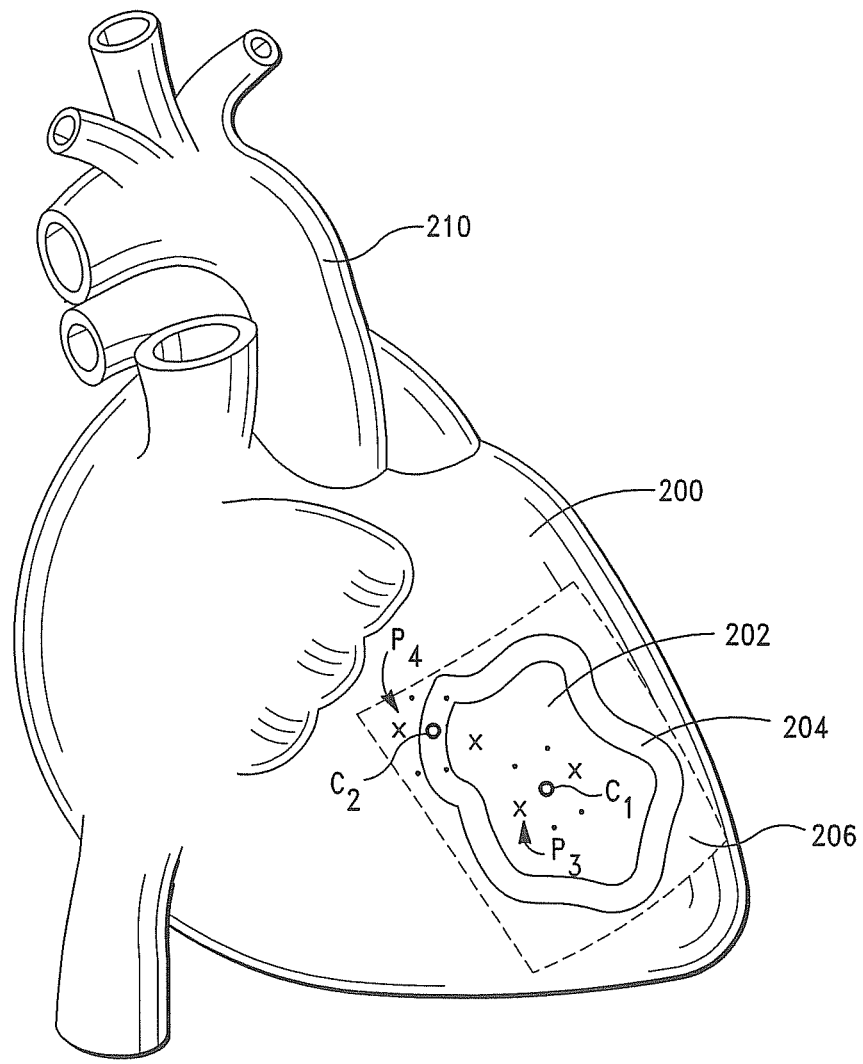
FIG. 14 is an illustration of an ischemic infarcted region of a heart with further embodiments of TMR/incited tissue/composition delivery patterns, in accordance with the invention.

Referring now to FIG. 14, there is shown an ischemic infarcted region 202 having multiple similar composition delivery/incited tissue/TMR impact region patterns (denoted "$P_3$" and "$P_4$") comprising TMR impact regions $C_1$ and $C_2$ and a radial arrangement of four (4) composition delivery regions (denoted ".") and two (2) incited tissue regions (denoted by "x"), according to one embodiment of the invention.

As illustrated in FIG. 14, composition delivery/incited tissue/TMR impact region pattern $P_3$ is disposed in the ischemic infarcted region 202 and composition delivery/incited tissue/TMR impact region pattern $P_4$ is partially disposed in the ischemic infarcted region 202, peri-infarcted region 204 and tissue proximate the peri-infarcted region 204.

Figure 15:
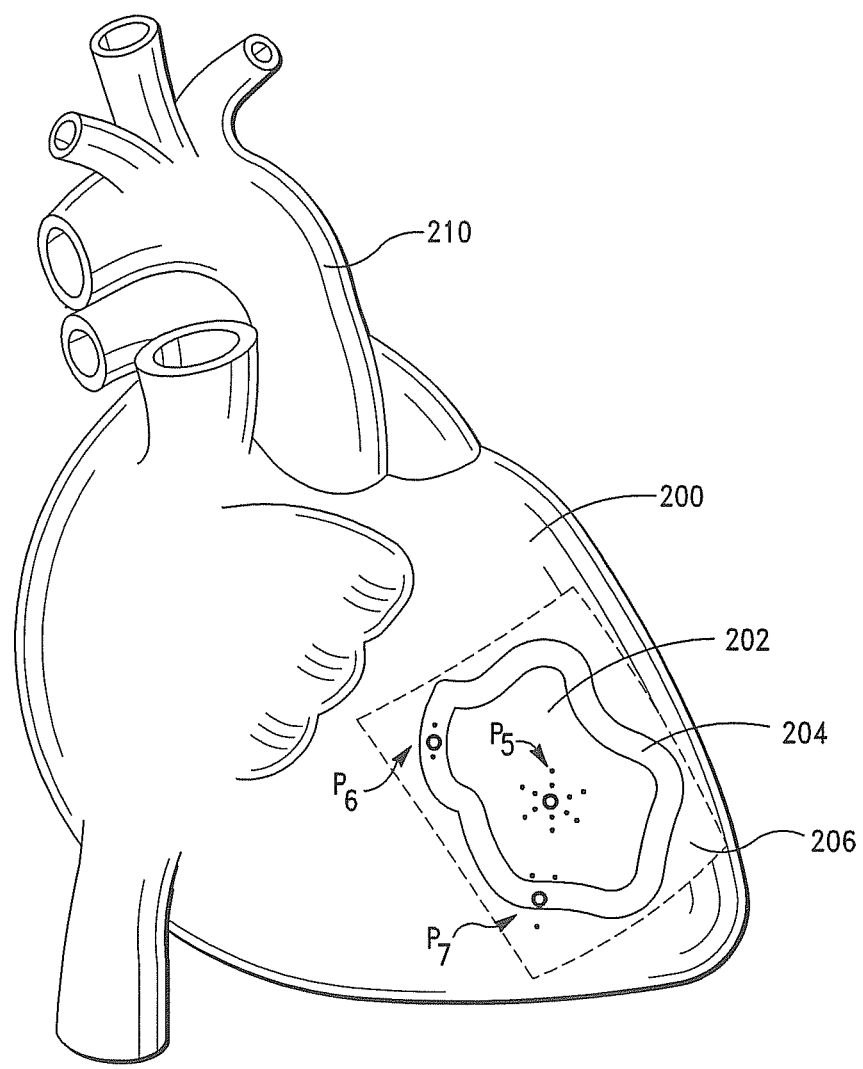
FIG. 15 is an illustration of an ischemic infarcted region of a heart with further embodiments of TMR/composition delivery patterns, in accordance with the invention.

Further exemplar composition delivery/incited tissue/TMR impact region patterns $P_5$, $P_6$, $P_7$ are shown in FIG. 15.

Referring now to FIG. 8, there is shown another embodiment of a TMR delivery method of the invention (denoted "20E"). As illustrated in FIG. 8, the TMR delivery method 20E similarly comprises the provision and use of an ECM based composition 10, composition delivery means and TMR means. However, in this embodiment, the composition delivery means and TMR means are provided via a joint TMR/composition delivery system 18b, comprising a composition delivery component 19a and TMR means component 19b.

In one embodiment of the invention, the joint TMR/composition delivery system 18b comprises a base multi-needle injection apparatus, such as the apparatus described in U.S. application Ser. No. 14/031,630, and an energy transmission apparatus.

Referring first to FIGS. 3A and 3B, as set forth in U.S. application Ser. No. 14/031,630, the base injection apparatus 300 includes (i) a first housing 302a having a needle array 304, and a plurality of reservoirs 306 contained therein, and ($i_1$) a second housing 302c having a plurality of reservoir piston drive members 308 and driving force receiving means 310.

As illustrated in FIG. 3A, the proximal end of the second housing 302c further includes a plurality of threads 310 that are configured to threadably receive (and cooperate with) internal threads of the housing retainer 312, whereby the housing retainer 312 securely engages the first 302a and second 302c housings together when the housing retainer 312 is engaged to (and tightened on) the second housing threads 310.

Further details regarding the base injection apparatus 300 are set forth in U.S. application Ser. No. 14/031,630.

Figure 3C:
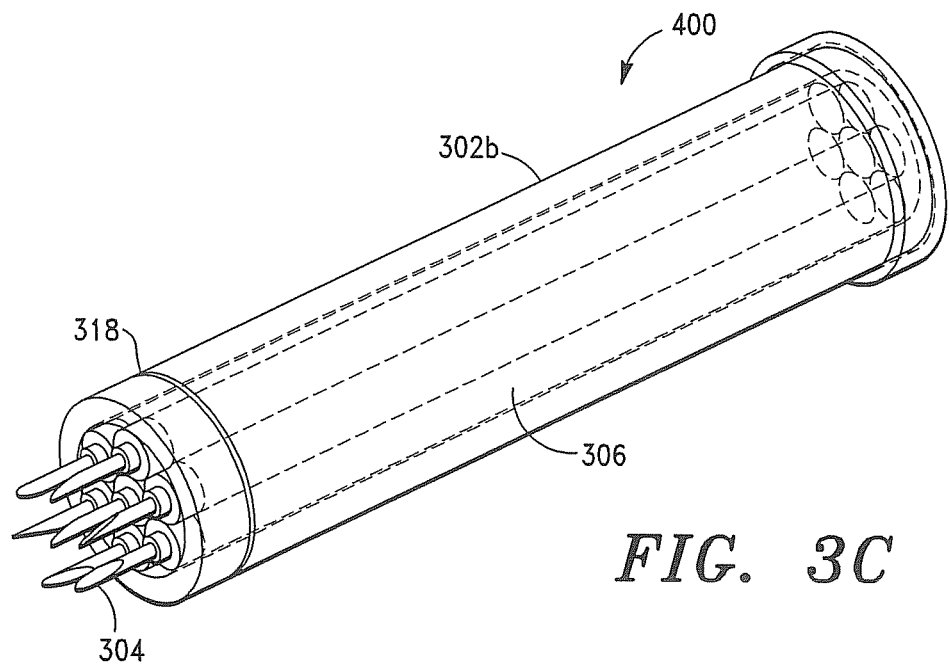
FIG. 3C is a perspective view of a housing member for one embodiment of a joint TMR/composition delivery system; in accordance with the invention.
Figure 3D:
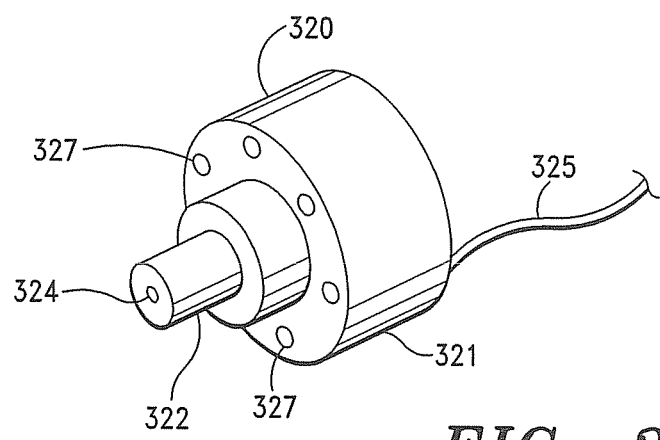
FIG. 3D is a perspective view of one embodiment of an energy transmission member that is configured to cooperate with the housing member shown in FIG. 3C; in accordance with the invention.

Referring now to FIGS. 3B, 3C and 3D, one embodiment of a joint TMR/composition delivery system 18b will be described in detail. According to the invention, the joint TMR/composition delivery system 18b comprises the second housing 302c and housing retainer 312 shown in FIG. 3A, a modified first housing 302b and an energy transmission member 320.

As illustrated in FIG. 3C, the modified first housing 302b similarly comprises a needle array 304 and a plurality of reservoirs 306 contained therein. However, in the joint TMR/composition delivery system 18b, the needle array 304 preferably does not include a center needle 305. The modified first housing 302b also includes a recessed region 318 disposed circumferentially proximate the proximal end of the first housing 302b, which is adapted to receive a retainer ring of energy transmission member 320 discussed below.

Referring now to FIG. 3D, the energy transmission member 320 comprises a housing 321 having an open internal region that is sized and configured to slidably engage the proximal end of the first housing 302b. The energy transmission member 320 further includes an internal retainer ring (not shown) that is sized and configured to engage the recessed region 318 on the first housing 302b when the energy transmission member 320 is seated thereon.

As illustrated in FIG. 3D, the energy transmission member 320 further includes an energy transmission port 322 having a lumen therethrough 324 that is sized and configured to receive and transmit energy therefrom, and a plurality of lumens 327 that are sized, configured and positioned to receive needles of the array 304 when the energy transmission member 320 is operatively positioned on the first housing 302b.

In a preferred embodiment of the invention, the energy transmission port 322 is adapted to receive light energy, more preferably, $CO_2$ laser energy, transmitted thereto via energy transmission line 325 and transmit the light energy to target tissue.

According to the invention, the light energy can be transmitted target tissue, such as damaged cardiovascular tissue associated with an ischemic infarcted region, simultaneously, jointly or in conjunction with (as defined herein) the administration or delivery of an ECM based composition of the invention.

According to the invention, the needle array 304 can similarly comprise various number of needles, e.g. 2 needles, 3 needles, 5 needles, etc. The needle array 304 can also comprise various spacings of the needles, as discussed above.

As further illustrated in FIGS. 7 and 8, when the ECM based ECM composition 10 is delivered to an ischemic infarcted region 202 and, hence, damaged cardiovascular tissue associated therewith, simultaneously, jointly or in conjunction with TMR means, i.e. 18a and/or 18b, the damaged cardiovascular tissue 202 is similarly remodeled and new cardiovascular tissue is regenerated 204.

There is thus described herein:
improved bioactive compositions and methods for treating damaged or diseased biological tissue; particularly, cardiovascular tissue and, hence, cardiovascular disorders associated therewith;
improved ECM based compositions that promote tissue survival, and induce neovascularization and regeneration of damaged cardiovascular tissue;
methods for treating cardiovascular disorders that include administration of improved ECM based compositions, which, when delivered to damaged cardiovascular tissue, induce neovascularization, host tissue proliferation, bioremodeling of the damaged cardiovascular tissue, and regeneration of new cardiovascular tissue and associated structures with site-specific structural and functional properties; and
methods for treating cardiovascular disorders that include administration of an ECM based composition to damaged cardiovascular tissue in conjunction with a treatment remedy, such as ventricular assistance and/or transmyocardial revascularization (TMR), which induces enhanced bioremodeling of the damaged cardiovascular tissue and regeneration of new cardiovascular tissue and associated structures with site-specific structural and functional properties.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A method for treating damaged cardiovascular tissue of a subject, the method comprising the steps of:

providing a mixed liquid exosome augmented extracellular matrix (ECM) composition, said exosome augmented ECM composition comprising acellular ECM from a mammalian tissue source and a plurality of exogenous exosomes isolated from mesenchymal stem cells (MSCs), said acellular ECM adapted to induce a first level of stem cell proliferation, bioremodeling of damaged cardiovascular tissue and regeneration of new cardiovascular tissue, when said acellular ECM is disposed proximate said damaged cardiovascular tissue, said plurality of exogenous exosomes adapted to induce a second level of stem cell proliferation, bioremodeling of said damaged cardiovascular tissue and regeneration of new cardiovascular tissue, when said plurality of exogenous exosomes is disposed proximate said damaged cardiovascular tissue;

providing a left ventricular assist device (LVAD) that supports heart function by reducing mechanical load on a left ventricle of a subject's heart when said LVAD is in communication with said subject's left ventricle; and delivering said exosome augmented ECM composition proximate said damaged cardiovascular tissue associated with said subject's cardiovascular disorder in conjunction with providing said support of said subject's heart function with said LVAD, wherein, a third level of stem cell proliferation, bioremodeling of said damaged cardiovascular tissue and regeneration of new cardiovascular tissue is induced, said third level of induced stem cell proliferation, bioremodeling of said damaged cardiovascular tissue and regeneration of new cardiovascular tissue being greater than the sum of said first level of induced stem cell proliferation, bioremodeling of said damaged cardiovascular tissue and regeneration of new cardiovascular tissue, and said second level of induced stem cell proliferation, bioremodeling of said damaged cardiovascular tissue and regeneration of new cardiovascular tissue.

2. The method of claim 1, wherein said mammalian tissue source comprises mammalian tissue selected from the group consisting of small intestine submucosa, urinary bladder submucosa, stomach submucosa, cardiac tissue, placental tissue, omentum tissue and kidney tissue.

3. The method of claim 1, wherein said plurality of exogenous exosomes comprise an encapsulated growth factor selected from the group consisting of exogenous bFGF, TGF-β, and VEGF.

4. The method of claim 1, wherein said plurality of exogenous exosomes comprise an encapsulated inflammation modulating agent selected from the group consisting of an interleukin, transcription factor RNA and micro RNA (miRNA).

5. The method of claim 1, wherein said delivery of said exosome augmented ECM composition and said provision of said heart function support are performed within a first period of time of less than 10 minutes of each other.

6. The method of claim 1, wherein said method further comprises the step of providing a needle-based injection system that is adapted to induce a biological insult in tissue when in communication therewith.

7. The method of claim 6, wherein said biological insult is induced in said damaged cardiovascular tissue with said needle-based injection system in conjunction with said delivery of said exosome augmented ECM composition and said provision of said heart function support.

8. The method of claim 7, wherein said biological insult comprises piercing said subject's damaged cardiovascular tissue.

9. The method of claim 7, wherein said delivery of said exosome augmented ECM composition, said induced biological insult and said heart function support are performed within a first period of time in the range of 5-60 minutes of each other.

* * * * *